(12) United States Patent
Brünner et al.

(10) Patent No.: US 11,903,927 B2
(45) Date of Patent: Feb. 20, 2024

(54) COMBINATION TREATMENT OF CANCER

(71) Applicant: Scandion Oncology A/S, Copenhagen N (DK)

(72) Inventors: Nils Aage Brünner, Hellerup (DK); Palle Christophersen, Ballerup (DK); Jan Stenvang, Copenhagen K (DK); Jens Lichtenberg, Græsted (DK); Annemette Thougaard, Kongens Lyngby (DK)

(73) Assignee: Scandion Oncology A/S, Copenhagen N (DK)

( * ) Notice: Subject to any disclaimer, the term of this patent is extended or adjusted under 35 U.S.C. 154(b) by 285 days.

(21) Appl. No.: 17/388,208

(22) Filed: Jul. 29, 2021

(65) Prior Publication Data

US 2021/0353596 A1 Nov. 18, 2021

Related U.S. Application Data

(62) Division of application No. 16/302,195, filed as application No. PCT/EP2017/061823 on May 17, 2017, now Pat. No. 11,103,481.

(30) Foreign Application Priority Data

May 17, 2016 (DK) .............................. PA201670325

(51) Int. Cl.
| | |
|---|---|
| *A61K 31/41* | (2006.01) |
| *A61P 35/00* | (2006.01) |
| *A61K 33/243* | (2019.01) |
| *A61K 31/138* | (2006.01) |
| *A61K 31/337* | (2006.01) |
| *A61K 31/495* | (2006.01) |
| *A61K 31/513* | (2006.01) |
| *A61K 31/566* | (2006.01) |
| *A61K 31/4745* | (2006.01) |
| *C07D 257/04* | (2006.01) |

(52) U.S. Cl.
CPC ............ *A61K 31/41* (2013.01); *A61K 31/138* (2013.01); *A61K 31/337* (2013.01); *A61K 31/4745* (2013.01); *A61K 31/495* (2013.01); *A61K 31/513* (2013.01); *A61K 31/566* (2013.01); *A61K 33/243* (2019.01); *A61P 35/00* (2018.01); *C07D 257/04* (2013.01)

(58) Field of Classification Search
CPC ........ A61K 31/41; A61K 31/138; A61P 35/00
See application file for complete search history.

(56) References Cited

U.S. PATENT DOCUMENTS

| 7,855,211 B2 | 12/2010 | Coates et al. | |
| 11,103,481 B2 * | 8/2021 | Brünner ................ | A61K 33/243 |

FOREIGN PATENT DOCUMENTS

| EP | 321122 A | * 6/1989 | ........... C07D 491/22 |
| EP | 1526851 A2 | 5/2005 | |
| EP | 2919009 A1 | 9/2015 | |
| EP | 3064207 A1 | 9/2016 | |
| WO | 1998/47879 | 10/1998 | |
| WO | 2000/24707 A1 | 5/2000 | |
| WO | 2004/012733 A2 | 2/2004 | |
| WO | 2004/111017 A1 | 12/2004 | |
| WO | 2005/075479 A1 | 8/2005 | |
| WO | 2006/064015 A2 | 6/2006 | |
| WO | 2007/104719 A1 | 9/2007 | |

OTHER PUBLICATIONS

American Cancer Society 2015; Chemotherapy Drugs: How They Work, 17 pages, Feb. 6, 2015.
Awada et al., Phase I trial to investigate the safety, pharmacokinetics and efficacy of sorafenib combined with docetaxel in patients with advanced refractory solid tumours, European Journal of Cancer, 48(4): 465-474, Jan. 27, 2012.
Daudigeos-Dubus et al., Regorafenib antitumor activity upon mono and combination therapy in preclinical pediatric malignancy models, PLOS ONE, 10(11): e0142612, Nov. 23, 2015.
Helix et al., Inhibition of the Endogenous Volume-regulated Anion Channel (VRAC) in HEK293, J. Membrane Biol., 196: 83-94, 2003.
Lethert et al. 2012; Fulvestrant (F) plus sorafenib (S) as salvage therapy for hormone receptor positive (HR+) metastatic breast cancer (MBC) failing prior aromatase inhibitor (AI) treatment, Journal of Clinical Oncology, 30(15): Suppl. 1, e11042, May 1, 2012.
Mross et al., Results from an in vitro and a clinical/pharmacological phase I study with the combination irinotecan and sorafenib, European Journal of Cancer, 43: 55-63, 2007.
Pedersen et al., Sorafenib and nilotinib resensitize tamoxifen resistant breast cancer cells to tamoxifen treatment via estrogen receptor [alpha], International Journal of Oncology, 45: 2167-2175, Aug. 22, 2014.
Planells-Cases et al., Subunit composition of VRAC channels determines substrate specificity and cellular resistance to Pt-based anti-cancer drugs, The EMBO Journal, 34(24):2993-3008, 2015.
Poulsen et al., Deregulation of apoptotic volume decrease and ionic movements. Am J Physiol Cell Physiol, 298: C14-C25, 2010.
Samalin et al., Sorafenib and irinotecan (NEXIRI) as a second- or later-line treatment for patients with metastatic colorectal cancer and KRAS-mutated tumours: a multicentre Phase I/II trial, British Journal of Cancer, 110(5):1148-1154, Jan. 9, 2014.
Schmieder et al., Regorafenib (BAY 73-4506) antitumor and antimetastatic activities in preclinical models of colorectal cancer: antitumor and antimetastatic activities of regorafenib. International Journal of Cancer, 135(6): 1487-1496, Sep. 15, 2014.

(Continued)

*Primary Examiner* — Kevin E Weddington
(74) *Attorney, Agent, or Firm* — Julie K. Staple; Dinsmore & Shohl, LLP

(57) ABSTRACT

The present invention relates to treatment of cancer, in particular to methods of sensitising cancer cells to an anti-cancer therapy by administering an effective amount of a modulator of Volume Regulated Anion Channels, i.e. a VRAC modulator.

19 Claims, 14 Drawing Sheets

(56) References Cited

OTHER PUBLICATIONS

Sørensen et al., Downregulation of LRRC8A protects human ovarian and alveolar carcinoma cells against Cisplatin-Induced expression of p53, MDM2, p21Waf1/Cip1, and Caspase-9/-3 activation, Am J Physiol Cell Physiol., 310: C857-C873, 2016.

Stenvang et al., DEN-50R—establishment of a novel and unique cell line based drug screening platform for cancer treatment, AACR-NCI-EORTC Symposium: Molecular Targets and Cancer Therapeutics, Abstract #B71, Sep. 24, 2015.

Stenvang et al., The volume regulated anion channel inhibitor NS3728 to enhance the cytotoxic effects of SN-38 in human colorectal cancer cells grown in vitro, Journal of Clinical Oncology, 34(15): suppl, E23170, May 20, 2016.

Sun et al., Phase II study of Sorafenib in combination with Docetaxel and Cisplatin in the treatment of metastatic or advanced gastric and gastroesophageal junction adenocarcinoma: ECOG 5203, Journal of Clinical Oncology, 28(18): 2947-2951, Jun. 20, 2010.

Wang et al., FOLFIRI and regorafenib combination therapy with dose escalation of irinotecan as fourth-line treatment for patients with metastatic colon cancer according to UGT1A1 genotyping, Oncotargets and Therapy, pp. 2143-2146, Nov. 1, 2014.

English translation of Office Action for Japanese Application No. 2018-560218, dated Apr. 13, 2021, 4 pages.

* cited by examiner

COMBINATION TREATMENT OF CANCER

REFERENCE TO RELATED APPLICATIONS

This application is a divisional of U.S. patent application Ser. No. 16/302,195, filed Nov. 16, 2018, which is U.S. national stage application of PCT/EP2017/061823, filed May 17, 2017, which claims priority from Danish application No. PA201670325, filed May 17, 2016. The entire content of each application is incorporated herein by reference.

FIELD OF THE INVENTION

The present invention relates to treatment of cancer, in particular to methods of sensitising cancer cells to an anti-cancer treatment by administering an effective amount of a VRAC modulator.

BACKGROUND OF THE INVENTION

Cancer is an overwhelming burden to our society with approximately 14 million new cases of cancer diagnosed in 2014. Despite the introduction of many new treatment modalities/options, de novo or acquired resistance to the applied treatments still represents the major cause of death from cancer.

Volume Regulated Anion Channels (VRACs) are present in most mammalian cells. An important function of VRAC is cell volume regulation. Upon swelling of the cell in hypotonic solution these channels are activated and chloride ions flow out of the cell in parallel with potassium ions (via potassium channels) and water, thereby restoring the original cell volume.

Compounds capable of blocking the activity of VRAC are characterised in Helix et al., J. Membrane Biol. 196 (2003). For example, NS3728 (Endovion; SCO-101) is a potent orally active VRAC blocker.

WO 98/47879 and WO 00/24707 disclose VRAC modulators, including NS3728, and their use in the treatment of sickle cell anaemia.

WO 2004/012733 discloses VRAC modulators, including NS3728, and their use in the treatment of diseases responsive to anti-angiogenic therapy, in particular anti-metastatic treatment.

Previous studies have indicated a role for VRAC in the ability of cancer cells to undergo apoptosis and NS3728 has been shown to inhibit cisplatin mediated apoptosis in vitro (Poulsen et al., Am J Physiol Cell Physiol, 2010; Sørensen et al., Am J Physiol Cell Physiol, 2016; Planells_Cases, R. et al., EMBO J., 2015).

Chemotherapeutic treatment of metastatic colorectal cancer (mCRC) is generally based on the anti-metabolite drug 5-fluorouracil (5FU) combined with either the DNA-binding agent oxaliplatin (e.g. FOLFOX regimen) or the topoisomerase I inhibitor irinotecan (e.g. FOLFIRI regimen) and often administered in combination with biological treatment, e.g. EGFR targeting drugs or anti-angiogenic drugs. Notwithstanding the efficacy of these combination regimens, which have significantly increased the response rate and survival of mCRC patients (Cunningham et al., 2010; Gallagher and Kemeny, 2010), only 30 to 50% of treated patients show an objective response to either of the combination therapies and progression of the cancer despite chemotherapy treatment is a common outcome (Gallagher and Kemeny, 2010; Goldberg et al., 2004). To make it even worse, the objective response rate to second line chemotherapy treatment of mCRC FOLFOX to prior FOLFIRI treated patients and vice versa is reduced to 10-20% and objective response to third line treatment is almost not existing. It is thus clear that de novo (pre-existing) or acquired drug resistance constitute the major problem in the management of mCRC. Similar conclusions can be drawn when discussing primary CRC where a large proportion (30-40%) of stage Ill patients receiving adjuvant chemotherapy (most often FOLFOX or XELOX) will present disease recurrence subsequent to the chemotherapy.

Breast cancer (BC) is a heterogeneous disease which is also reflected in a heterogeneous response pattern to various types of chemotherapy. In adjuvant treatment of BC the most often used drugs are cytotoxic drugs including anthracyclines (topoisomerase 2 inhibitors) and taxanes. These drugs are most often administered in conjunction with cyclophosphamide. For patients with estrogen receptor positive BC, adjuvant treatment most often includes anti-estrogens such as aromatase inhibitors, estrogen receptor antagonists (tamoxifen and fulvestrant). However, approximately 18-20% of patients receiving adjuvant or neoadjuvant systemic anti-cancer treatment will experience a disease recurrence. In patients with metastatic BC (mBC) response rates to systemic therapy range from 60% in first line treatment with a rapid decrease to 20-25% when reaching $3^{rd}$ to $4^{th}$ line treatment. These figures clearly indicate a high degree of both de novo resistance and acquired resistance leading to disease progression and the death of thousands of women every year.

It follows that identification, characterisation and preclinical and clinical validation of new drugs and drug combinations for treatment of cancer and in particular drug resistant cancer constitute a highly unmet medical need.

SUMMARY OF THE INVENTION

The present invention provides a novel treatment regimen for cancer and is particularly suitable for treatment of chemotherapy-resistant cancers. The treatment regimen of the present invention comprises treatment with a compound capable of modulating the activity of volume regulated anion channels (VRAC), i.e. a VRAC modulator, such as Endovion (NS3728). Co-treatment with a VRAC modulator has surprisingly been shown to enhance the effect of an anti-cancer treatment. Further, co-treatment with a VRAC modulator is shown to be capable of re-sensitising chemotherapy resistant cancer cells to treatment with certain chemotherapeutic agents.

In a first aspect the present invention relates to a method of sensitising cancer cells to an anti-cancer treatment comprising administering to a subject in need thereof an effective amount of a VRAC modulator. The VRAC modulator may be administered before, during and/or after the anti-cancer treatment is administered.

In a second aspect the present invention relates to a method of potentiating the therapeutic effect of an anti-cancer treatment comprising administering to a subject in need thereof an effective amount of a VRAC modulator. The VRAC modulator may be administered before, during and/or after the anti-cancer treatment is administered.

In a third aspect the present invention relates to a method for treatment of cancer comprising administering to a subject in need thereof an effective amount of a VRAC modulator and an effective amount of an anti-cancer treatment, such as a chemotherapeutic agent.

In a fourth aspect the present invention relates to a composition comprising an effective amount of a VRAC modulator and a chemotherapeutic agent.

In a fifth aspect the present invention relates to a composition comprising an effective amount of a VRAC modulator and an effective amount of a chemotherapeutic agent for use as a medicament.

In a sixth aspect the present invention relates to a composition comprising an effective amount of a VRAC modulator and an effective amount of a chemotherapeutic agent for use in the treatment of cancer.

In a seventh aspect the present invention relates to a VRAC modulator for use in sensitising cancer cells to an anti-cancer treatment.

In an eighth aspect the present invention relates to a VRAC modulator for use in potentiating the therapeutic effect of an anti-cancer treatment.

In a ninth aspect the present invention relates to a kit of parts comprising a VRAC modulator and a chemotherapeutic agent, wherein the VRAC modulator and the chemotherapeutic agent are formulated for simultaneous, sequential or separate administration and optionally instructions for use.

In a tenth aspect the present invention relates to use of a VRAC modulator for the manufacture of a medicament for sensitising cancer cells to an anti-cancer treatment or for use in potentiating the therapeutic effect of an anti-cancer treatment.

In an eleventh aspect the present invention relates to use a VRAC modulator and an anti-cancer therapy, such as a chemotherapeutic agent, for treatment of a patient wherein said patient has previously been determined to be resistant to treatment with said anti-cancer agent.

DETAILED DESCRIPTION OF THE INVENTION

Figure 1:
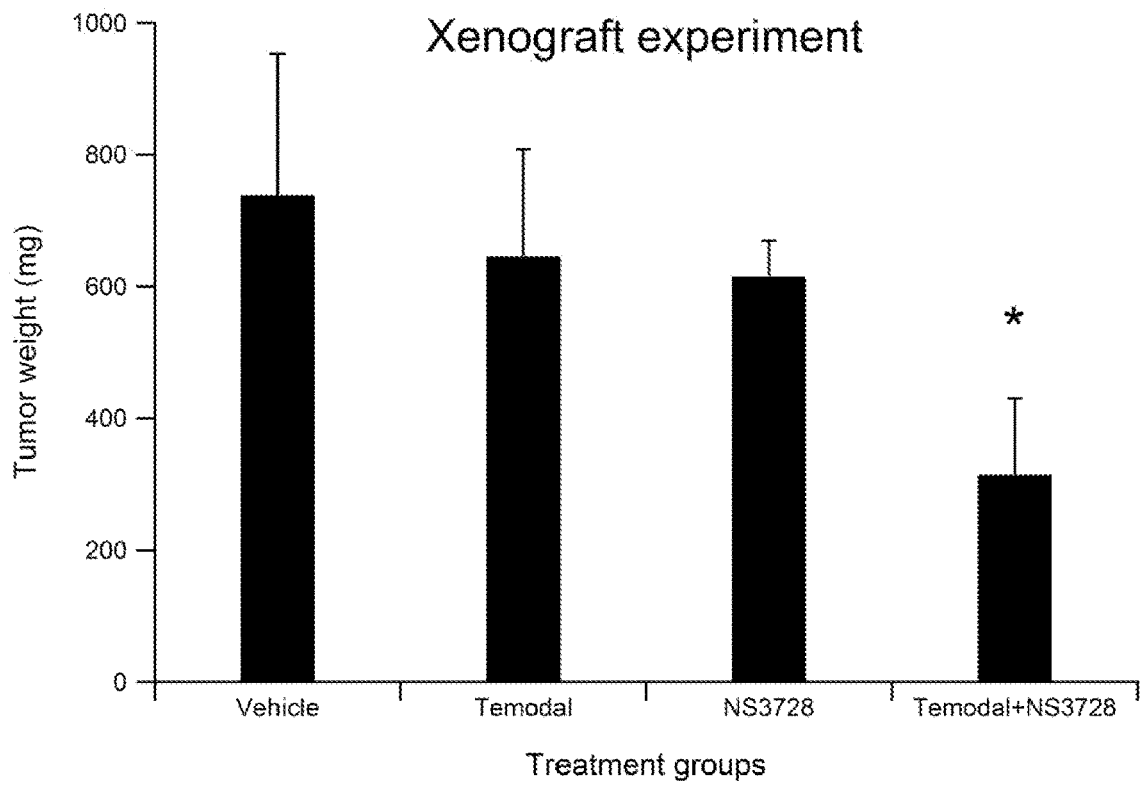
FIG. 1. Effect of daily doses of NS3728 (40 mg/kg PO), temozolamide (Temodal) (25 mg/kg IP), and the combination thereof on the growth of C9 glioblastoma xenografts in vivo.

The present inventors have surprisingly found that co-treatment of cancer with a VRAC modulator and an anti-cancer therapy, such as a chemotherapeutic agent, has increased efficacy as compared to monotherapy, and furthermore re-sensitises chemoresistant cancer cells to treatment, and therefore propose a new treatment regimen for cancer wherein a VRAC modulator is administered to potentiate the therapeutic effect of an anti-cancer treatment and/or sensitise the cancer cells to the anti-cancer treatment.

VRAC

Volume regulated anion channels (VRAC) are present in most mammalian cells. An important function of VRAC is cell volume regulation: Upon swelling of the cell in hypotonic solution these channels are activated and chloride ions flow out of the cell in parallel with potassium ions (via potassium channels) and water, thereby restoring the original cell volume.

The gene family encoding the VRACs was identified essentially simultaneously by two independent groups in 2014 as being the LRRC8 family (Voss et al, 2014, Science 344(6184):634-8 and Qui et al, 2014, Cell 157(2):447-58). VRAC has also in the literature historically been known as Volume-Sensitive Organic Osmolyte Anion Channel (VSOAC), Volume Sensitive Outward Rectifier (VSOR), Voltage Dependent Anion Channel (VDAC), Human Volume-Sensitive Outward Rectifier (HSVOR), Volume Regulated Chloride Channel (VRCIC) and $I_{Cl,swell}$. These phenotypical manifestations are currently assumed to be the result of different compositions of LRRC8 subunits in the functional VRAC expressed in different cell types.

VRAC is an almost ubiquitously distributed anion channel, which is activated by cell swelling and/or a decrease in intracellular ionic strength. It is the channel mediating increased anion conductance during Regulatory Volume Decrease (RVD). In electrophysiological recordings VRAC exhibits outward rectification and in most cells a pronounced voltage-dependent inactivation at positive membrane potentials. VRAC is highly anion selective with a unique selectivity sequence for small inorganic ions: $SCN^-<I^-=NO_3^-<Br^-<Cl^-<HCO_3^-<F^-$ (Eisenman type I halide selectivity sequence) and—depending on the specific subunit composition—having a wide pore that also allows the permeation of a large number of negatively charged or neutral organic molecules such as cisplatin.

Activation of VRAC is obligatory dependent on the presence of intracellular ATP and complex intracellular signalling cascades involving protein kinases support the activation process.

VRAC Blocker

In one embodiment, the VRAC modulator is a VRAC blocker. The term "VRAC blocker" is used interchangeably herein with the term "VRAC inhibitor". A VRAC blocker is a compound that inhibits the transmembrane transport of chloride or any other anion or neutral molecule in response to cell swelling or decrease in intracellular ionic strength.

A compound acting as a VRAC inhibitor binds to the channel protein and exerts its inhibiting effect discernible via one or more of the methods of measuring VRAC function as described herein. Inhibiting compounds may act via one or more theoretical mode-of-actions (MOA), the main groups of which are:

1) A way to obtain inhibition is by directly obstructing (blocking) the current flow through the open channel by binding somewhere in the transmembrane pore region of the channel. Such molecules are sometimes referred to as "blockers" in the art.

2) Another—much more heterogeneous way—to obtain inhibition is by preventing or delaying the channel's natural activation processes and/or by stimulating/accelerating its natural inactivation or deactivation processes. Such molecules are expected overall to result in a lowered probability of finding an individual channel protein in its open configuration (lowered open state probability, Po). Such molecules may be mentioned collectively as "negative gating modulators", no matter which microscopic processes they influence. A negative gating modulator is also sometimes referred to as a "negative allosteric modulator" or a "NAM".

The elucidation of the detailed MOA for a particular compound is a very challenging task, and may require a combination of high-sensitivity functional measurements (e.g. single channel recordings as mentioned herein) and high-resolution structural information (e.g. crystallography, sequence analyses, mutagenesis analyses etc.). In the present case it is not unequivocally determined which MOAs are responsible for the VRAC inhibiting effects of the VRAC modulators mentioned herein. Thus, they are collectively referred to as VRAC blockers.

The potential of a given substance to act as a VRAC blocker may be determined using standard laboratory test methods, such as a) whole cell or single channel patch clamp technology, or the automatic HTC versions of the same
b) microelectrode electrophysiology (penetrating, sharp electrodes),
c) flux assays (e.g. radioactive as well as non-radioactive isotopes),
d) fluorescent dyes (e.g. membrane potential—or chloride concentration indicators),
e) cell volume measurements (e.g. light scattering, coulter counter measurements, or optical methods such as image analysis).

To measure VRAC activity it is necessary to activate the channel protein by swelling the cell (e.g. by exposure to a hypotonic extracellular Ringers solution) or by making the intracellular solution hypertonic or low in ionic strength (only few technologies allow that, i.e. the whole cell patch clamp describes under 1.a below) VRAC activity is most directly registered by electrophysiological methods that allow direct measurements of the swelling activated transmembrane anion current at a fixed membrane potential (voltage clamp). The possibilities are:

Manual Techniques a) Manual whole cell patch clamp (measurement of the anion current from the entire cell membrane). This is the most realistic configuration for drug screening. The cell attached configuration (measurement of the current through relatively few ion channels expressed in a tiny piece of the cell membrane) has been used in a few cases in the literature, and the same counts for the excised configurations, where the membrane fragments have been isolated on the tip of the patch pipette (inside out and outside out configurations). These methods are mostly relevant in biophysical investigations or in the elucidation of mode-of-action of specific compounds (low throughput).

b) Perforated patch recordings (essentially the same configuration as the whole cell configuration described under 1a, with the difference that there is not established a hole in the membrane, however a low resistance connection to the cell interior by using permeabilizing agents (typically bacterial pore forming peptides, such as amphotericin B). The throughput is considerably lower that the whole cell method but has the advantage of keeping the cellular milieu closer to the physiological composition during recording. (In the context of VRAC, which depends on intracellular ATP, this molecule does not need to be applied to the pipette solution as it has in the whole cell configuration).

c) Manual "classical" electrophysiology using membrane penetrating "sharp" electrodes. Not easily implemented for drug screening, since the method is very difficult to use with typical small laboratory cell lines (HEK, CHO etc.) Automatic techniques d) Various forms of HTS electrophysiology, which today is exemplified by QPatch or QUBE from Sophion Bioscience (Korsgaard, M P et al, Comb Chem High Troughput Screen, 2009; Chambers, C et al, Assay Drug Dev Technol., 2016) or the Nanion systems. All methods are basically doing whole cell measurements (see a) or perforated patch measurements (see b) using a flat glass or silicon substrate mounted on a chip, which allow a high degree or automatization of measurements and compound/fluid handling in a parallel set up.

More indirect effects of VRAC activation can be measured by:

a) Expression (either stably, transiently, or inducible) of a halide-sensitive fluorescent protein or peptide in the cell in question (i.e. HEK293). Most used is yellow fluorescent protein (YFP), the light emission of which is extremely sensitive to the type and concentration of halides in the medium. In this context it is exploited that the effect of the iodide ion is much more pronounced than the chlorine ion. By applying iodide ions, (which are more permeable trough VRAC than the Cl ions) to the extracellular solution it is achieved that these pass the membrane into the cell interior when VRAC opens (in the opposite direction of the chlorine ions leaving the cell). Thereby the VRAC activation is reported by the increased light emission from YFP. Inhibitors of VRAC are expected to dampen this emission (less iodide ion influx) and the method can thus be used for quantification of the potency and degree of inhibition.

b) The degree of swelling of the cells which express VRAC can be followed directly by measuring the cell size, for example by a coulter counter, light scattering techniques, microscopic techniques or impedance measurements. VRAC inhibition will not affect the swelling process, but will prevent or delay the volume recovery process called RVD (regulatory volume decrease) which is driven by VRAC activation. It is important to realize that by measuring both YFP and cell size one increasingly relies on indirect "downstream" effects of VRAC activation, which significantly increases the risk of registering both false positive and false negative signals. Such results are therefore usually validated by use of electrophysiology measurements.

c) Many other methods can be coupled to VRAC activation, but these are even more indirect. Effects in migration, proliferation, cytotoxicity, apoptosis assays on special cell lines may all be important in their own rights with respect to prediction of in vivo cancer effects, but none are only dependent on VRAC.

VRAC expression can be measured for example by qPCR, in situ hybridization or antibodies.

In one embodiment the VRAC blocker is a diphenyl urea derivative such as those described in WO 98/47879 and/or WO 00/24707.

In one embodiment, the VRAC blockers show IC50-values of less than 10 µM, such as less than 1000 nM, for example less than 100 nM, such as less than 50 nM, for example less than 10 nM for in vitro inhibition according to the standard test methods.

In one embodiment, the VRAC blocker has an IC50 of 5 µM or less, such as 3 µM or less, for example 1 µM or less, such as 0.5 µM or less, for example 0.1 µM or less, such as 10 nM or less, for example 5 nM or less.

In one embodiment, the VRAC blocker has an IC50 of 2 µM or less, such as 1 µM or less, such as 0.5 µM or less, for example 0.1 µM or less, such as 10 nM or less, for example 5 nM or less. In a preferred embodiment, the VRAC blocker has an IC50 of 0.5 µM or less.

One example of a VRAC blocker is a compound of general formula I

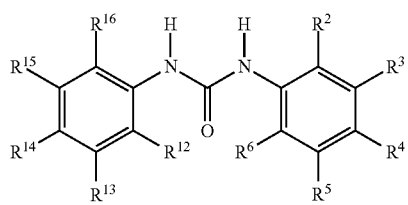

or a pharmaceutically acceptable salt thereof
wherein $R^2$ represents tetrazolyl; and
$R^3$, $R^4$, $R^5$, $R^6$, $R^{12}$, $R^{13}$, $R^{14}$, $R^{15}$, and $R^{16}$ independently of each other represent hydrogen, halo, trifluoromethyl, nitro, alkyl, alkylcarbonyl, —$NR^aR^b$, —$NR^a$—CO—$R^b$, phenyl or heteroaryl; which phenyl is optionally substituted with halo, trifluoromethyl, nitro, —CO—$NHR^c$, —CO—O—$R^c$ or —CO—NR'R";
wherein $R^c$ is hydrogen, alkyl, or phenyl;
R' and R" independently of each other are hydrogen or alkyl; or
R' and R" together with the nitrogen to which they are attached form a 5- to 7-membered heterocyclic ring, which ring may optionally comprise as a ring member, one oxygen atom, and/or one additional nitrogen atom, and/or one carbon-carbon double bond, and/or one carbon-nitrogen double bond;
and which heterocyclic ring may optionally be substituted with alkyl;
$R^a$ and $R^b$ independently of each other are hydrogen or alkyl; or
$R^{15}$ and $R^{16}$, or $R^{14}$ and $R^{15}$ together with the phenyl ring to which they are attached form a naphthyl ring or an indanyl ring; and $R^3$, $R^4$, $R^5$, $R^6$, $R^{12}$ and $R^{13}$ and the remaining one of $R^{14}$, $R^{15}$ and $R^{16}$ are as defined above.

In one embodiment, the VRAC blocker is a compound of general formula I

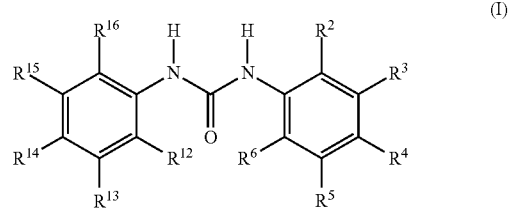

or a pharmaceutically acceptable salt thereof,
wherein $R^2$ represents tetrazolyl;
$R^3$, $R^4$, $R^5$, $R^6$, $R^{12}$, $R^{13}$, $R^{14}$, $R^{15}$, and $R^{16}$ independently of each other represent hydrogen, halo, trifluoromethyl, nitro, or phenyl;
which phenyl is optionally substituted with halo, trifluoromethyl, nitro, or —CO—$NHR^c$; wherein $R^c$ is hydrogen, alkyl, or phenyl.

In one embodiment the compound of general formula I, $R^2$ represents tetrazolyl; $R^3$, $R^4$, $R^5$, $R^6$, $R^{12}$, $R^{13}$, $R^{14}$, $R^{15}$, and $R^{16}$ independently of each other represent hydrogen, halo, trifluoromethyl, or nitro.

In one embodiment the compound of general formula I, $R^3$, $R^5$, and $R^6$ represent hydrogen; and $R^4$ represents halo, such as bromine.

In one embodiment the compound of general formula I, $R^3$, $R^4$, $R^5$ and $R^6$ represent hydrogen.

In a further embodiment of the compound of general formula I, $R^3$, $R^5$, and $R^6$ represent hydrogen; and $R^4$ represents —$NR^aR^b$, such as amino.

In a still further embodiment of the compound of general formula I, $R^3$, $R^5$, and $R^6$ represent hydrogen; and $R^4$ represents —$NR^a$—CO—$R^b$, such as acetylamino.

In a further embodiment of the compound of general formula I, $R^3$, $R^5$, and $R^6$ represent hydrogen; and $R^4$ represents phenyl substituted with trifluoromethyl, nitro or —CO—$NHR^c$; wherein $R^c$ is phenyl. In a special embodiment, $R^4$ represents phenyl substituted with trifluoromethyl, such as 4-trifluoromethylphenyl. In a further embodiment, $R^4$ represents phenyl substituted with nitro, such as 3-nitrophenyl. In a further embodiment, $R^4$ represents phenyl substituted with —CO—$NHR^c$, such as anilinocarbonylphenyl, in particular 4-anilinocarbonylphenyl.

In a further embodiment of the compound of general formula I, $R^3$, $R^5$, and $R^6$ represent hydrogen; and $R^4$ represents phenyl substituted with —CO—O—$R^c$ or —CO—NR'R". In a special embodiment, $R^4$ represents phenyl substituted with —CO—O—$R^c$, wherein $R^c$ is hydrogen. In a special embodiment, R4 represents phenyl substituted with —CO—NR'R", such as 4-dimethylcarbamoylphenyl or 4-(4-methyl-1-piperazine-carbonyl)-phenyl.

In a still further embodiment, $R^{15}$ represents trifluoromethyl. In a special embodiment, $R^{15}$ represents trifluoromethyl and $R^{12}$, $R^{13}$, $R^{14}$ and $R^{16}$ represent hydrogen. In a further embodiment $R^{13}$ represents trifluoromethyl. In a special embodiment, $R^{13}$ and $R^{15}$ represent trifluoromethyl and $R^{12}$, $R^{14}$ and $R^{16}$ represent hydrogen.

In a further embodiment, $R^{16}$ represents trifluoromethyl. In a special embodiment, $R^{16}$ represents trifluoromethyl and $R^{12}$, $R^{13}$, $R^{14}$ and $R^{15}$ represent hydrogen.

In a still further embodiment, $R^{15}$ represents halo, such as chloro or bromo. In a special embodiment, $R^{15}$ represents halo, such as chloro or bromo, and $R^{12}$, $R^{13}$, $R^{14}$ and $R^{16}$ represent hydrogen. In a further embodiment, $R^{13}$ and $R^{15}$ represent halo, such as chloro, and $R^{12}$, $R^{14}$ and $R^{16}$ represent hydrogen. In a still further embodiment, $R^{14}$ and $R^{15}$ represent halo, such as chloro, and $R^{12}$, $R^{13}$ and $R^{16}$ represent hydrogen.

In a further embodiment, $R^{16}$ represents halo, such as fluoro. In a special embodiment, $R^{16}$ represents halo, such as fluoro, and $R^{12}$, $R^{13}$, $R^{14}$ and $R^{15}$ represent hydrogen.

In a still further embodiment, $R^{16}$ represents alkyl, such as methyl or ethyl. In a special embodiment, $R^{16}$ represents alkyl, such as methyl or ethyl, and $R^{12}$, $R^{13}$, $R^{14}$ and $R^{15}$ represent hydrogen.

In a further embodiment, $R^{14}$ represents nitro. In a special embodiment, $R^{14}$ represents nitro, and $R^{12}$, $R^{13}$, $R^{15}$ and $R^{16}$ represent hydrogen.

In a still further embodiment, $R^{14}$ represents alkylcarbonyl, such as acetyl. In a special embodiment, $R^{14}$ represents alkylcarbonyl, such as acetyl, and $R^{12}$, $R^{13}$, $R^{15}$ and $R^{16}$ represent hydrogen.

In a further embodiment, $R^{15}$ represents phenyl. In a further embodiment, $R^{14}$ represents phenyl. In a special embodiment, one of $R^{14}$ or $R^{15}$ represents phenyl, and the remaining of $R^{12}$, $R^{13}$, $R^{14}$, $R^{15}$ and $R^{16}$ represent hydrogen.

In a still further embodiment, $R^{15}$ represents pyridyl, such as pyridin-3-yl. In a special embodiment, $R^{15}$ represents pyridyl, such as pyridin-3-yl, and $R^{12}$, $R^{13}$, $R^{14}$ and $R^{16}$ represent hydrogen.

In a further embodiment, $R^{15}$ and $R^{16}$ together with the phenyl ring to which they are attached form a naphthyl ring.

In a still further embodiment, $R^{14}$ and $R^{15}$ together with the phenyl ring to which they are attached form an indanyl ring.

In a further embodiment, the compound of general formula I is selected from
N-4-Nitrophenyl-N'-[4-bromo-2-(1-H-tetrazol-5-yl)phenyl] urea;
N-3,5-Di(trifluoromethyl)phenyl-N'-[4-bromo-2-(1-H-tetrazol-5-yl)phenyl] urea;
N-3-Trifluoromethylphenyl-N'-[4-(3-nitrophenyl)-2-(1-H-tetrazol-5-yl)phenyl] urea;
N-3-Trifluoromethylphenyl-N'-[4-(4-anilinocarbonylphenyl)-2-(1-H-tetrazol-5-yl)phenyl] urea;
N-3-Trifluoromethylphenyl-N'-[4-(4-trifluoromethylphenyl)-2-(1-H-tetrazol-5-yl)phenyl] urea;
N-(3-Trifluoromethyl-phenyl)-N'-[2-(1-H-tetrazol-5-yl)-phenyl] urea;
N-(3-Trifluoromethyl-phenyl)-N'-[4-bromo-2-(1-H-terazol-5-yl)-phenyl] urea;
N-(3-Trilfuoromethyl-phenyl)-N'-[4-phenyl-2-(1-H-tetrazol-5-yl)-phenyl] urea;
N-(3-Chloro-phenyl)-N'-[2-(1-H-tetrazol-5-yl)-phenyl] urea;
N-(3-Trifluoromethyl-phenyl)-N'-[4-amino-2-(1-H-tetrazol-5-yl)-phenyl] urea;
N-(3-Trifluoromethyl-phenyl)-N'-[4-acetylamino-2-(1-H-tetrazol-5-yl)-phenyl] urea;
N-(3-Trilfuoromethyl-phenyl)-N'-[4-carbamoyl-2-(1-H-tetrazol-5-yl)-phenyl] urea;
N-(3-Trifluoromethyl-phenyl)-N'-[4-(N",N"-dimethylcarbamoyl)-2-(1-H-tetrazol-5-yl)-phenyl]urea;
3'-(1-H-tetrazol-5-yl)-4'-[3-(3-trifluoromethyl-phenyl)-ureido]-biphenyl-4-carboxylic acid;
N-(Indan-5-yl)-N'-[2-(1-H-tetrazol-5-yl)-phenyl] urea;
N-(Biphenyl-4-yl)-N'-[2-(1-H-tetrazol-5-yl)-phenyl] urea;
N-(Biphenyl-3-yl)-N'-[2-(1-H-tetrazol-5-yl)-phenyl] urea;
N-(3-Acetyl-phenyl)-N'-[2-(1-H-tetrazol-5-yl)-phenyl] urea;
N-(Biphenyl-3-yl)-N'-[2-(1-H-tetrazol-5-yl)-phenyl] urea;
N-[3-(Pyridin-3-yl)-phenyl]-N'-[2-(1-H-tetrazol-5-yl)-phenyl] urea;
N-(3-Bromo-phenyl)-N'-[4'-(4-methyl-piperazine-1-carbonyl)-3-(1-H-tetrazol-5-yl)-biphenyl-4-yl] urea;
N-(3,5-Dichloro-phenyl)-N'-[4-bromo-2-(1-H-tetrazol-5-yl)-phenyl] urea;
N-(3,4-Dichloro-phenyl)-N'-[4-bromo-2-(1-H-tetrazol-5-yl)-phenyl] urea;
N-(Naphthalen-1-yl)-N'-[4-bromo-2-(1-H-tetrazol-5-yl)-phenyl] urea;
N-(2-Trifluoromethyl-phenyl)-N'-[4-bromo-2-(1-H-tetrazol-5-yl)-phenyl] urea;
N-(2-Fluoro-phenyl)-N'-[4-bromo-2-(1-H-tetrazol-5-yl)-phenyl] urea;
N-(2-Ethyl-phenyl)-N'-[4-bromo-2-(1-H-tetrazol-5-yl)-phenyl] urea;
or a pharmaceutically acceptable salt thereof.

In a special embodiment of the invention, the compound is
N-4-Nitrophenyl-N'-[4-bromo-2-(1-H-tetrazol-5-yl)phenyl] urea;
N-3,5-Di(trifluoromethyl)phenyl-N'-[4-bromo-2-(1-H-tetrazol-5-yl)phenyl] urea;
N-3-Trifluoromethylphenyl-N'-[4-(3-nitrophenyl)-2-(1-H-tetrazol-5-yl)phenyl] urea;
N-3-Trifluoromethylphenyl-N'-[4-(4-anilinocarbonylphenyl)-2-(1-H-tetrazol-5-yl)phenyl] urea;
N-3-Trifluoromethylphenyl-N'-[4-(4-trifluoromethylphenyl)-2-(1-H-tetrazol-5-yl)phenyl] urea;
or a pharmaceutically acceptable salt thereof, In one embodiment the VRAC blocker is NS3728:

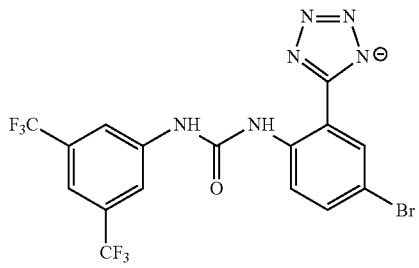 [SMILES: O=C(Nc1cc(C(F)(F)F)cc(C(F)(F)F)c1)Nc1ccc(Br)cc1-c1nnn[n-]1]

or a pharmaceutically acceptable salt thereof. NS3728 is also known as Endovion and SCO-101. NS3728 is a potent orally active VRAC blocker with an $IC_{50}$ of 0.40 µM (Helix et al., J Membrane Biol. 196, 2003).

In one embodiment the VRAC blocker is NS3623:

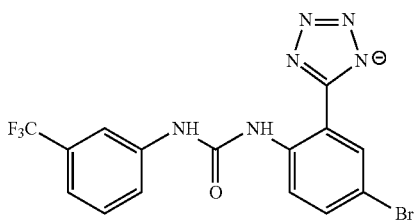 [SMILES: O=C(Nc1cccc(C(F)(F)F)c1)Nc1ccc(Br)cc1-c1nnn[n-]1]

or a pharmaceutically acceptable salt thereof. NS3623 is a VRAC blocker with an $IC_{50}$ of 1.8 µM (Helix et al., J Membrane Biol. 196, 2003).

In one embodiment the VRAC blocker is NS3749:

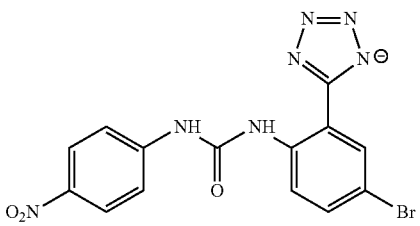 [SMILES: O=C(Nc1ccc([N+](=O)[O-])cc1)Nc1ccc(Br)cc1-c1nnn[n-]1]

or a pharmaceutically acceptable salt thereof. NS3749 is a VRAC blocker with an $IC_{50}$ of 1.4 µM (Helix et al., J Membrane Biol. 196, 2003).

In one embodiment, the VRAC blocker is tamoxifen (TMX):

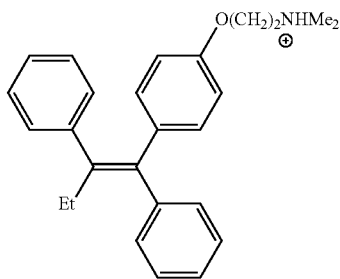

or a pharmaceutically acceptable salt thereof. Tamoxifen is a medication that is used to prevent breast cancer in women and treat breast cancer in women and men. It is also being studied for other types of cancer. Tamoxifen is a voltage-dependent blocker of VRAC with an $IC_{50}$=2.2 µM (Helix et al., J Membrane Biol. 196, 2003).

In one embodiment the VRAC blocker is not tamoxifen. In particular, when the anti-cancer treatment is an anti-estrogen, more particularly tamoxifen, the VRAC blocker is not tamoxifen.

Other examples of VRAC blockers include DIDS ($IC_{50}$=26 µM) and NPPB ($IC_{50}$=21 µM) (Helix et al., J Membrane Biol. 196, 2003).

In one embodiment the VRAC modulator is identified as described in EP 2 919 009, the teaching of which is incorporated by reference in its entirety.

Definition of Substituents

In the context of the present disclosure halo represents fluoro, chloro, bromo or iodo.

In the context of present disclosure an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In one embodiment alkyl represents a $C_{1-4}$-alkyl group, including butyl, isobutyl, secondary butyl, and tertiary butyl. In another embodiment of this invention alkyl represents a $C_{1-3}$-alkyl group, which may in particular be methyl, ethyl, propyl or isopropyl.

In the context of present disclosure a heteroaryl group designates an aromatic mono-, bi- or poly-heterocyclic group, which holds one or more heteroatoms in its ring structure. Preferred heteroatoms include nitrogen (N), oxygen (O), and sulphur (S). Preferred monocyclic heteroaryl groups of the invention include aromatic 5- and 6 membered heterocyclic monocyclic groups, including furanyl, in particular 2- or 3-furanyl; thienyl, in particular 2 or 3-thienyl; pyrrolyl (azolyl), in particular 1,2 or 3-pyrrolyl; oxazolyl, in particular oxazol-2,4 or 5-yl; thiazolyl, in particular thiazol-2,4 or 5-yl; imidazolyl, in particular 1,2 or 4-imidazolyl; pyrazolyl, in particular 1,3 or 4-pyrazolyl; isoxazolyl, in particular isoxazol-3,4 or 5-yl; isothiazolyl, in particular isothiazol-3,4 or 5-yl; oxadiazolyl, in particular 1,2,3-, 1,2,4-, 1,2,5- or 1,3,4-oxadiazol-3,4 or 5-yl; triazolyl, in particular 1,2,3-, 1,2,4-, 2,1,3- or 4,1,2-triazolyl; thiadiazolyl, in particular thiadiazol-3,4 or 5-yl; pyridinyl, in particular 2,3 or 4-pyridinyl; pyridazinyl, in particular 3 or 4-pyridazinyl; pyrimidinyl, in particular 2,4 or 5-pyrimidinyl; pyrazinyl, in particular 2 or 3-pyrazinyl; and triazinyl, in particular 1,2,3-, 1,2,4- or 1,3,5-triazinyl.

5- to 7-membered heterocyclic rings comprising one nitrogen atom include for example, but not limited to, pyrolidine, piperidine, homopiperidine, pyrroline, tetrahydropyridine, pyrazolidine, imidazolidine, piperazine, homopiperazine, and morpholine.

Pharmaceutically Acceptable Salts

The VRAC blocker as described herein may be provided in any form suitable for the intended administration. Suitable forms include pharmaceutically (i.e. physiologically) acceptable salts, and pre- or prodrug forms.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzen-sulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound for use according to the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts (aza-onium salts). Preferred aza-onium salts include the alkyl-onium salts, in particular the methyl- and the ethyl-onium salts; the cycloalkyl-onium salts, in particular the cyclopropyl-onium salts; and the cycloalkylalkyl-onium salts, in particular the cyclopropylmethyl-onium salts.

Pharmaceutical Compositions

In one embodiment the present invention relates a pharmaceutical composition comprising an effective amount of a VRAC modulator and a chemotherapeutic agent.

While the VRAC blocker and/or the chemotherapeutic agent as disclosed herein may be administered in the form of the raw chemical compounds, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In one embodiment, the invention provides pharmaceutical compositions comprising the VRAC blocker according to the invention, or a pharmaceutically acceptable salt or derivative thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof. In a further embodiment, the invention provides pharmaceutical compositions comprising more than one compound or prodrug for use according to the invention, such as two different compounds or prodrugs for use according to the invention.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The VRAC blocker of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The VRAC blocker as disclosed herein can be administered in a wide variety of oral and parenteral dosage forms.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The VRAC blocker according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the VRAC blocker may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the VRAC blocker may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier. Solutions or suspensions may be applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatine, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronisation.

When desired, compositions adapted to give sustained release of the VRAC active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

In other embodiments the VRAC inhibitor is formulated for topical administration.

Further details on techniques for formulation and administration may be found in the latest edition of Remington's Pharmaceutical Sciences (Maack Publishing Co, Easton, PA).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage of the VRAC modular and/or the anti-cancer agent depends on the nature and severity of the disease being treated, and is within the discretion of the physician, and may be varied by titration of the dosage to the particular circumstances to produce the desired therapeutic effect.

For example the VRAC blocker may be administered in one or several doses per day. Exemplary ranges are from 10-200 mg/day p.o. (per oral) administered in one or two doses, such as from 25-50 mg p.o. twice a day.

The subject to be treated according to the present disclosure may be any human or animal subject, preferably a human suffering from cancer.

Cancer

The present invention relates to sensitising cancer cells to an anti-cancer treatment or potentiating the therapeutic effect of an anti-cancer treatment.

In one embodiment the cancer is resistant to treatment with a chemotherapeutic agent. If a cancer is resistant, co-treatment with a VRAC blocker is capable of re-sensitising the cancer to the chemotherapeutic agent in question. Resistance of cancers may be either de novo resistance or acquired resistance. In general, a cancer is regarded as resistant to a particular anti-cancer therapy if a patient treated with the clinically accepted dosage of the anti-cancer agent does not respond as expected to the anti-cancer agent, i.e. in case of worsening, growth, or spread of the cancer (progressive disease). Whether a cancer is drug-sensitive or resistant can be determined by the skilled person.

In one embodiment, the cancer to be treated according to the present disclosure may be selected from the group consisting of lung cancer (non small cell lung cancer and small cell lung cancer), Glioblastomas, Head and neck cancers, Malignant melanomas, Basal cell skin cancer, Squamous cell skin cancer, Breast cancer, Liver cancer, Pancreatic cancer, Prostate cancer, Colorectal cancer, anal cancer, Cervix uteri cancer, Bladder cancer, Corpus uteri cancer, Ovarian cancer, Gall bladder cancer, Sarcomas, Leukemia's (myeloid and lymphatic), Lymphomas, Myelomatosis.

In one embodiment the cancer is metastatic.

In one embodiment the cancer is colorectal cancer.

In one embodiment the cancer is metastatic colorectal cancer.

In one embodiment the cancer is breast cancer.

In one embodiment the cancer is metastatic breast cancer.

In one embodiment the cancer is glioblastoma.

In one embodiment the cancer is a solid tumour such as a solid tumour selected from sarcoma, carcinoma and lymphoma.

In one embodiment the cancer is not a solid tumour. For example, the cancer may be a hematological malignancy including but not limited to leukemia.

In one embodiment the cancer is prostate cancer, such as metastatic prostate cancer.

In one embodiment the cancer is a steroid hormone receptor positive cancer, e.g. an estrogen receptor positive cancer, a progesterone receptor positive cancer or an androgen receptor positive cancer.

Anti-Cancer Treatments

An anti-cancer treatment according to the present disclosure may be treatment with one or more chemotherapeutic agents and/or radiation therapy. In a preferred embodiment, the anti-cancer treatment encompasses treatment with a chemotherapeutic agent.

Chemotherapy drugs can be divided into groups based on factors such as how they work, their chemical structure, and their relationship to other drugs. Some drugs act in more than one way, and may belong to more than one group. In one embodiment the anti-cancer treatment of the present invention encompasses treatment with more than one chemotherapeutic agent.

In one embodiment, the anti-cancer treatment is a chemotherapeutic agent selected from the group consisting of a cytotoxic agent, a cytostatic agent, an anti-hormone agent, an anti-angiogenic agent and an anti-cancer biologic agent with a well-defined target.

In one embodiment, the chemotherapeutic agent is a cytotoxic agent or a cytostatic agent.

In a preferred embodiment, the anti-cancer treatment is a chemotherapeutic agent and the VRAC modulator is co-administered with the chemotherapeutic agent.

The VRAC modulator may be administered prior to, simultaneously with and/or after initiation of the anti-cancer treatment. In one embodiment the VRAC modulator is administered prior to initiation of anti-cancer treatment. In one embodiment the VRAC modulator is administered simultaneously with the anti-cancer treatment.

Co-administration as used herein refers to administration of a VRAC modulator and an anti-cancer treatment to a subject, wherein the VRAC modulator may be administered prior to, simultaneously with and/or after the anti-cancer treatment.

Administration of a VRAC modulator potentiates the effect of the anti-cancer treatment. Thus, the effect of treatment with a VRAC blocker and an anti-cancer treatment is additive or synergistic. In one embodiment, the effect of treatment is synergistic.

In one embodiment administration of the VRAC modulator allows for administration of the anti-cancer treatment at a lower than normal dose, i.e. a dose that would normally be considered a sub-therapeutic dosage.

In one embodiment administration of the VRAC modulator enhances the clinical effect of the anti-cancer treatment. Clinical effect may be determined by the clinician.

In one embodiment, the anti-cancer treatment is a chemotherapeutic agent selected from the group consisting of topoisomerase inhibitors, anti-hormone agents, alkylating agents, antimetabolites, anti-tumour antibiotics, mitotic inhibitors, corticosteroids, targeted anti-cancer therapies, differentiating agents, and immunotherapy.

Alkylating Agents

In one embodiment the chemotherapeutic agent is an alkylating agent. Alkylating agents directly damage DNA (the genetic material in each cell) to keep the cell from reproducing. These drugs work in all phases of the cell cycle and are used to treat many different cancers, including glioblastoma, leukemia, lymphoma, Hodgkin disease, multiple myeloma, and sarcoma, as well as cancers of the lung, breast, and ovary.

Alkylating agents are divided into different classes, including:

Nitrogen mustards: such as mechlorethamine (nitrogen mustard), chlorambucil, cyclophosphamide (Cytoxan®), ifosfamide, and melphalan Nitrosoureas: such as streptozocin, carmustine (BCNU), and lomustine Alkyl sulfonates: busulfan Triazines: dacarbazine (DTIC) and temozolomide (Temodar®)

Ethylenimines: thiotepa and altretamine (hexamethylmelamine)

In one embodiment the alkylating agent is selected from the group consisting of Nitrogen mustards, Nitrosoureas, Alkyl sulfonates, Triazines, Ethylenimine.

In one embodiment the alkylating agent is a triazine, such as temozolomide.

The platinum drugs (such as cisplatin, carboplatin, and oxaliplatin) are sometimes grouped with alkylating agents because they kill cells in a similar way. However, in the present context, platinum drugs are not considered alkylating agents.

In one embodiment the anti-cancer treatment does not comprise or consist of treatment with a metal-based anti-cancer drug, such as a platinum, ruthenium, gold or titanium-based anticancer drug.

In one embodiment the anti-cancer treatment does not comprise or consist of treatment with a platinum-based anticancer drug, such as cisplatin, carboplatin, oxaliplatin or nedaplatin.

In one embodiment, an alkylating agent is combined with a VRAC modulator for the treatment of glioblastoma, in particular glioblastoma, which is resistant to treatment with alkylating agents.

In a particular embodiment, the alkylating agent is a triazine, such temozolomide (temodal), the VRAC modulator is NS3728 and the cancer to be treated is glioblastoma, in particular temozolomide-resistant glioblastoma.

Antimetabolites

In one embodiment the chemotherapeutic agent is an antimetabolite. Antimetabolites interfere with DNA and RNA growth by substituting for the normal building blocks of RNA and DNA. These agents damage cells during the S phase, when the cell's chromosomes are being copied. They are commonly used to treat leukemias, cancers of the breast, ovary, and the intestinal tract, e.g. colorectal cancer as well as other types of cancer.

In one embodiment the antimetabolite is selected from the group consisting of 5-fluorouracil (5-FU), 6-mercaptopurine (6-MP), Capecitabine (Xeloda®), Cytarabine (Ara-C®), Floxuridine, Fludarabine, Gemcitabine (Gemzar®), Hydroxyurea, Methotrexate, Pemetrexed (Alimta®).

In one embodiment the antimetabolite is 5-fluorouracil (5-FU).

In one embodiment an anti-metabolite is combined with a VRAC modulator for the treatment of colorectal cancer, in particular colorectal cancer which is resistant to treatment with anti-metabolites. In one embodiment the colorectal cancer is metastatic colorectal cancer.

In a particular embodiment, 5-FU is co-administered with a VRAC modulator, such as NS3728, for the treatment of colorectal cancer, in particular a 5-FU resistant colorectal cancer. In one embodiment the colorectal cancer is metastatic colorectal cancer.

Anti-Tumour Antibiotics

These drugs work by altering the DNA inside cancer cells to keep them from growing and multiplying.

In one embodiment the chemotherapeutic agent is an anti-tumour antibiotic agent. In other embodiments, the chemotherapeutic agent is not an anti-tumour antibiotic agent.

In one embodiment the anti-tumour antibiotic agent is an anthracycline. Anthracyclines are anti-cancer antibiotics that interfere with enzymes involved in DNA replication. These drugs work in all phases of the cell cycle. They are widely used for a variety of cancers.

Anthracyclines are also capable of inhibiting topoisomerase II.

Examples of anthracyclines include:
Daunorubicin
Doxorubicin (Adriamycin®)
Epirubicin
Idarubicin
Anti-tumor antibiotics that are not anthracyclines include:
Actinomycin-D
Bleomycin
Mitomycin-C
Mitoxantrone (also acts as a topoisomerase II inhibitor)

Topoisomerase Inhibitors

In one embodiment the chemotherapeutic agent is a topoisomerase inhibitor, which may be a Topoisomerase I inhibitor or a Topoisomerase II inhibitor. These drugs interfere with enzymes called topoisomerases, which help separate the strands of DNA so they can be copied during the S phase. Topoisomerase inhibitors are used to treat colorectal cancer, certain leukemias, as well as lung, ovarian, gastrointestinal, and other cancers.

Topoisomerase inhibitors are grouped according to which type of enzyme they affect.

Topoisomerase I inhibitors include:
Topotecan
Irinotecan (CPT-11). The active metabolite of irinotecan is SN-38.
Topoisomerase II inhibitors include:
Etoposide (VP-16)
Teniposide.
Mitoxantrone (also acts as an anti-tumor antibiotic)
Anthracyclines In one embodiment the topoisomerase inhibitor is a Topoisomerase I inhibitor, such as Irinotecan or its active metabolite SN-38.

In one embodiment the topoisomerase inhibitor is a Topoisomerase II inhibitor, such as an anthracycline.

In one embodiment a topoisomerase inhibitor, such as a topoisomerase I inhibitor, is combined with a VRAC modulator for the treatment of colorectal cancer, in particular colorectal cancer which is resistant to treatment with said topoisomerase inhibitor. In one embodiment the colorectal cancer is metastatic colorectal cancer.

In a particular embodiment, irinotecan/SN-38 is co-administered with a VRAC modulator, such as NS3728, for the treatment of colorectal cancer, in particular an irinotecan/SN-38 resistant colorectal cancer. In one embodiment the colorectal cancer is metastatic colorectal cancer.

Mitotic Inhibitors

In one embodiment the chemotherapeutic agent is a mitotic inhibitor. Mitotic inhibitors are often plant alkaloids and other compounds derived from natural products. They work by stopping mitosis in the M phase of the cell cycle but can damage cells in all phases by keeping enzymes from making proteins needed for cell reproduction.

Examples of mitotic inhibitors include:
Taxanes: paclitaxel (Taxol®) and docetaxel (Taxotere®)
Epothilones: ixabepilone (Ixempra®)
Vinca alkaloids: vinblastine (Velban®), vincristine (Oncovin®), and vinorelbine (Navelbine®)
Estramustine (Emcyt®)

Mitotic inhibitors are used to treat many different types of cancer including breast, lung, myelomas, lymphomas, and leukemias.

In one embodiment the mitotic inhibitor is a taxane, such as paclitaxel or docetaxel.

In one embodiment a mitotic inhibitor is combined with a VRAC modulator for the treatment of breast cancer, in particular breast cancer which is resistant to treatment with mitotic inhibitors. In one embodiment the breast cancer is metastatic breast cancer.

In a particular embodiment, a taxane, such as paclitaxel or docetaxel is co-administered with a VRAC modulator, such as NS3728, for the treatment of breast cancer, in particular a paclitaxel or docetaxel resistant breast cancer. In one embodiment the breast cancer is metastatic breast cancer.

Corticosteroids

In one embodiment the chemotherapeutic agent is a corticosteroid. Corticosteroids, often simply called steroids, are natural hormones and hormone-like drugs that are useful in the treatment of many types of cancer, as well as other illnesses.

When these drugs are used as part of cancer treatment, they are considered chemotherapy drugs.

Examples of corticosteroids include:
Prednisone
Methylprednisolone (Solumedrol®)
Dexamethasone (Decadron®).

Steroids are also commonly used to help prevent nausea and vomiting caused by chemotherapy. They are used before chemotherapy to help prevent severe allergic reactions, too.

In some embodiments the chemotherapeutic agent is not a corticosteroid.

Other Chemotherapy Drugs

Some chemotherapy drugs act in slightly different ways and do not fit well into any of the other categories. Examples include drugs like L-asparaginase, which is an enzyme, and the proteasome inhibitor bortezomib (Velcade®).

Targeted Anti-Cancer Therapies

In one embodiment the chemotherapeutic agent is a targeted anti-cancer agent, such as an antibody-based therapy which acts on a well-defined target or biologic pathway.

Examples of targeted therapies include:
Imatinib (Gleevec®)
Gefitinib (Iressa®)
Sunitinib (Sutent®)
Bortezomib (Velcade®).

In one embodiment the targeted anti-cancer therapy is an anti-angiogenesis agent, such as an anti-VEGF agent. For instance, the anti-angiogenesis agent may be a humanised anti-VEGF monoclonal antibody, such as Avastin (Bevacizumab). If the anti-cancer therapy of the present disclosure is an anti-angiogenesis agent, the anti-angiogenesis agent is not a VRAC blocker such as NS3728.

In some embodiments the chemotherapeutic agent is not a targeted anti-cancer agent.

Differentiating Agents

These drugs act on the cancer cells to make them mature into normal cells. Examples include the retinoids, tretinoin (ATRA or Atralin®) and bexarotene (Targretin®), as well as arsenic trioxide (Arsenox®).

In one embodiment the chemotherapeutic agent is a differentiating agent. In some embodiments the chemotherapeutic agent is not a differentiating agent.

Anti-Hormone Agents

In one embodiment the chemotherapeutic agent is an agent for anti-hormone therapy. Drugs in this category are sex hormones, or hormone-like drugs, that change the action or production of female or male hormones. They are used to slow the growth of breast, prostate, and endometrial (uterine) cancers, which normally grow in response to natural sex hormones in the body. These cancer treatment hormones do not work in the same ways as standard chemotherapy drugs. They work by making the cancer cells unable to use the hormone they need to grow, or by preventing the body from making the hormone.

Examples of anti-hormone therapy include:
Anti-estrogens: fulvestrant (Faslodex®), tamoxifen, and toremifene (Fareston®), clomifene, and raloxifene.
Anti-progestogens: mifepristone, ulipristal acetate, aglepristone, lilopristone and onapristone
Anti-androgens: bicalutamide (Casodex®), flutamide (Eulexin®), and nilutamide (Nilandron®)
Aromatase inhibitors: anastrozole (Arimidex®), exemestane (Aromasin®), and letrozole (Femara®)
Progestins: megestrol acetate (Megace®)
Estrogens
Gonadotropin-releasing hormone (GnRH), also known as luteinizing hormonereleasing hormone (LHRH) agonists or analogs: leuprolide (Lupron®) and goserelin (Zoladex®).

In one embodiment, the anti-cancer treatment comprises anti-estrogen treatment. Anti-estrogens, also known as estrogen receptor antagonists or estrogen receptor blockers, are a class of drugs which prevent estrogens like estradiol from mediating their biological effects in the body.

In one embodiment, the anti-estrogen is fulvestrant.
In one embodiment the anti-estrogen is tamoxifen.

In one embodiment, the anti-cancer treatment comprises anti-progestogen treatment. Anti-progestogens, or anti-progestins, also known as progesterone receptor antagonists or progesterone blockers, are a class of drugs which prevent progestogens like progesterone from mediating their biological effects in the body.

Examples of anti-progestogens include mifepristone, ulipristal acetate, aglepristone, lilopristone and onapristone.

In one embodiment, the anti-cancer treatment comprises anti-androgen treatment. Anti-androgens, also known as androgen receptor antagonists or testosterone blockers, are a class of drugs which prevent androgens like testosterone and dihydrotestosterone (DHT) from mediating their biological effects in the body.

In some embodiments the chemotherapeutic agent is not an anti-hormone agent.

Anti-hormone therapy is particularly useful for treatment of steroid hormone receptor positive cancers, for example anti-estrogens are used for treatment of ER positive breast or uterine cancer.

In one embodiment, an anti-estrogen is co-administered with a VRAC modulator, such as NS3728, for the treatment of an ER positive cancer, such as an ER positive breast cancer. In one embodiment the breast cancer is metastatic breast cancer.

In one embodiment, an anti-progestogen is co-administered with a VRAC modulator, such as NS3728, for the treatment of a PR positive cancer, such as a PR positive breast cancer. In one embodiment the breast cancer is metastatic breast cancer.

In one embodiment, an anti-androgen is co-administered with a VRAC modulator, such as NS3728, for the treatment of an AR positive cancer, such as an AR positive prostate cancer. In one embodiment the prostate cancer is metastatic prostate cancer.

Immunotherapy

In one embodiment the chemotherapeutic agent is an immunotherapy agent. Immunotherapy drugs are given to people with cancer to help their immune systems recognize and attack cancer cells.

There are different types of immunotherapy. Active immunotherapies stimulate the body's own immune system to fight the disease. Passive immunotherapies do not rely on the body to attack the disease; they're immune system components (such as antibodies) created outside the body and given to fight the cancer.

Examples of active immunotherapies include:
Monoclonal antibody therapy, such as rituximab (Rituxan®) and alemtuzumab (Campath®)
Non-specific immunotherapies and adjuvants (other substances or cells that boost the immune response), such as BCG, interleukin-2 (IL-2), and interferon-alfa
Immunomodulating drugs, such as thalidomide and lenalidomide (Revlimid®)

In one embodiment the chemotherapeutic agent is a PD-1 or PD-L1 inhibitor, such as an antibody capable of inhibiting PD-1 or PD-L1.

Cancer vaccines are a type of active specific immunotherapy.

In some embodiments the chemotherapeutic agent is not an immunotherapy agent.

Radiation Therapy

In one embodiment the anti-cancer treatment is radiation therapy. Radiation therapy is therapy using ionizing radiation, generally as part of cancer treatment to control or kill malignant cells. Radiation therapy may be curative in a number of types of cancer if they are localized to one area of the body. It may also be used as part of adjuvant therapy, to prevent tumour recurrence after surgery to remove a primary malignant tumour (for example, early stages of breast cancer). Radiation therapy is synergistic with chemotherapy, and has been used before, during, and after chemotherapy in susceptible cancers. Doses and treatment schedules of radiation therapy vary depending on the type and stage of cancer being treated and can be determined by the clinician.

Medical Use

In one embodiment the present invention relates to a method of sensitising cancer cells to an anti-cancer treatment comprising administering to a subject in need thereof an effective amount of a VRAC modulator.

In one embodiment the present invention relates to a method of potentiating the therapeutic effect of an anticancer treatment comprising administering to a subject in need thereof an effective amount of a VRAC modulator.

In one embodiment the present invention relates to a method for treatment of cancer comprising administering to a subject in need thereof an effective amount of a VRAC modulator and an effective amount of an anti-cancer treatment, such as a chemotherapeutic agent.

In one embodiment the present invention relates to a composition comprising an effective amount of a VRAC modulator and an effective amount of a chemotherapeutic agent for use as a medicament.

In one embodiment the present invention relates to a composition comprising an effective amount of a VRAC modulator and an effective amount of a chemotherapeutic agent for use in the treatment of cancer.

In one embodiment the present invention relates to a VRAC modulator for use in sensitising cancer cells to an anti-cancer treatment.

In one embodiment the present invention relates to a VRAC modulator for use in potentiating the therapeutic effect of an anti-cancer treatment.

In one embodiment the present invention relates to use of a VRAC modulator for the manufacture of a medicament for sensitising cancer cells to an anti-cancer treatment or for use in potentiating the therapeutic effect of an anti-cancer treatment.

In one embodiment the present invention relates to a kit of parts comprising a VRAC modulator and a chemotherapeutic agent, wherein the VRAC modulator and the chemotherapeutic agent are formulated for simultaneous, sequential or separate administration and optionally instructions for use.

In a particularly interesting embodiment the present invention relates to a VRAC modulator and an anti-cancer therapy, such as a chemotherapeutic agent, for use in the treatment of cancer in a subject, wherein said cancer has been determined to be resistant to treatment with said anti-cancer therapy. Treatment with a VRAC modulator re-sensitises the resistant cancer cells to treatment with the anti-cancer therapy. The resistance may be de novo resistance or acquired resistance.

Co-treatment with the VRAC modulator as described herein may be considered an adjuvant therapy to an anti-cancer treatment as the VRAC modulator maximises the effectiveness of the anti-cancer therapy.

In one embodiment treatment with a VRAC modulator as described herein may be considered a neoadjuvant therapy when administered before the anti-cancer treatment.

EXAMPLES

Example 1. Temozolomide and NS3728 in Glioblastoma

The in vivo anti-tumor effect of NS3728 on C6 glioma cells given either as monotherapy (40 mg/kg/day) or in combination with temozolomide (Temodal, 25 or 5 mg/kg/day) was tested in two separate experiments, using either the xenograft method or the subcutaneous air sac model (SAS; see Lichtenberg, J., P. J. Hjarnaa, P. E. Kristjansen, D. Hansen & L. Binderup: The rat subcutaneous air sac mode: A quantitative assay of antiangiogenesis in induced vessels Pharmacology & Toxicology, 1999, 84, 34-40).

In the first study 5 million C6 rat glioma cells were inoculated into the flank of Fisher rats. Three days later the tumours had grown into a size of 2-5 mm in diameter and treatment was started. The C6 cells were observed to have aggressive growth behaviour and quickly marked solid tumours had been formed. Oral administration of NS3728 (40 mg/kg/day) in combination with temozolomide (25 mg/kg/day) resulted in a significant reduction of growth rate, whereas neither NS3728 (40 mg/kg/day) nor temozolomide (25 mg/kg/day) exhibited any significant anti-tumor effect when given as monotherapy (see FIG. 1). Clear signs of toxicity were observed in all animals treated with temozolomide and comprised of subdued behaviour, hunched appearance and loss of body weight. The study was terminated on day 4 of treatment due to ethical reasons.

Figure 2:
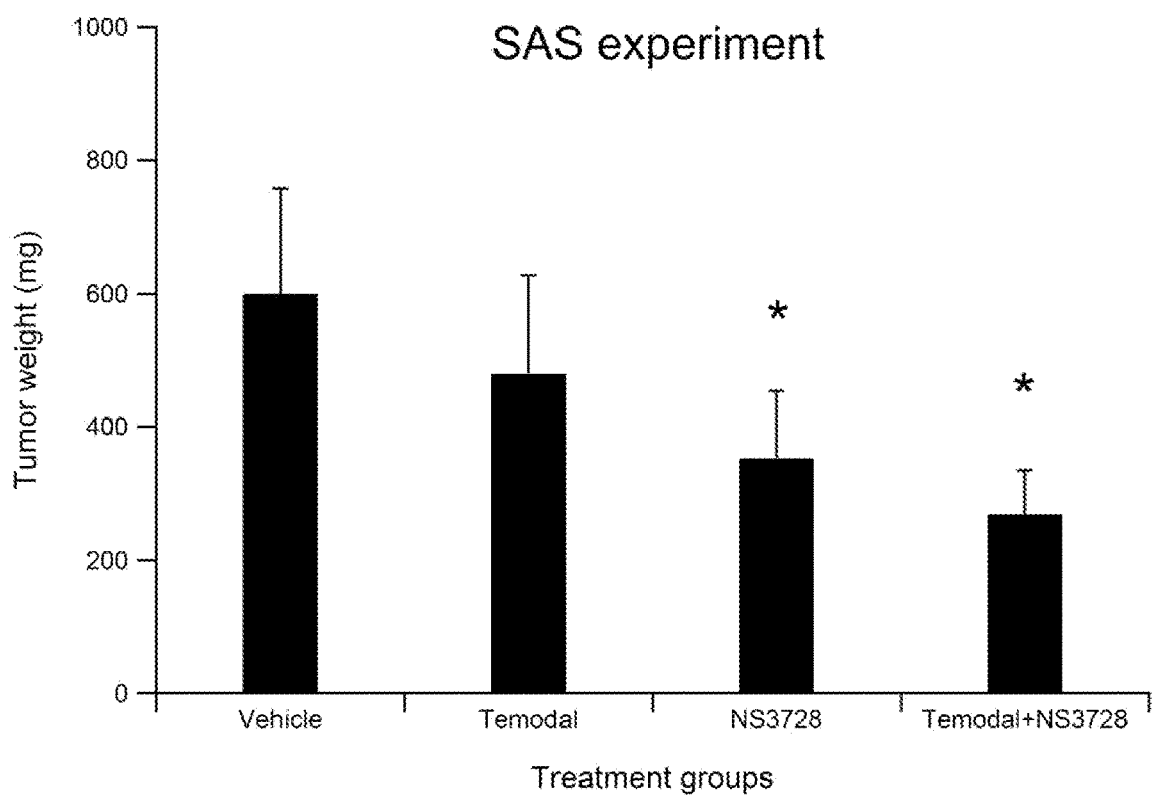
FIG. 2. Effect of daily doses of NS3728 (40 mg/kg) temozolamide (Temodal) (5 mg/kg IP), and the combination thereof on the growth of C9 glioblastoma cells in the subcutaneous airsac (SAS) model in vivo.

In the second study the tumour growth was retarded by inoculating only half the number of cells (2.5 million of C6 cells per animal) and making use of the subcutaneous air sac (SAS) technique. In brief, the rats were anaesthetized with $CO_2/O_2$ and 10-15 ml of air was introduced dorsally by subcutaneous injections to produce an air sac located approximately 4-5 cm behind the head. The wall of the air sac became progressively thicker with time and after 10-14 days a sufficient lining of cells with the appearance of a transparent membrane had been established. The C6 glioma cells were inoculated in the rats directly on the membrane. The treatment was started at the day of inoculation and the study was terminated on day 10 of treatment. The C6 cells exhibited less aggressive growth and oral administration of NS3728 (40 mg/kg/day) given either as monotherapy or in combination with temozolomide (5 mg/kg/day) produced a significant inhibition of tumour growth (FIG. 2) while treatment with temozolomide alone did not result in a significant tumour growth inhibition as measured by tumour weight.

The experiments presented here demonstrate that NS3728 dosed orally in combination with temozolomide ("first line" therapy against glioblastoma in Denmark) retards the growth of the C6 glioma cells by 50-55% independently of the site of inoculation. Compared to monotherapy with either compound the effects were clearly additive or synergistic. Thus, the results show that treatment with NS3728 sensitises cancer cells to treatment and potentiates the effect of temozolomide in vivo.

Example 2. Paclitaxel or 5-Flourouracil and NS3728 in Colon Cancer

The in vivo antitumor effect of NS3728 on the human HT29 colon cancer cell line were tested as monotherapy (80 mg/kg) respectively in combination with paclitaxel (5 mg/kg) or 5-flourouracil (30 mg/kg) in two independent experimental series. NS3728 was given per oral (PO), whereas both paclitaxel and 5-flourouracil were dosed intraperitoneally (IP) by injection. The cancer cells were inoculated subcutaneously at t=0 (one animal in the vehicle group did not develop a tumour and was excluded from the 5-flourouracil experiment), and treatments started at day 4 and ended at day 22. The experiments comprised the following dosing groups (n=9-10/group):
1) Vehicle,
2) NS3728,
3) paclitaxel or 5-flourouracil,
4) NS3728+paclitaxel or NS3728+5-flourouracil.

Figure 3:
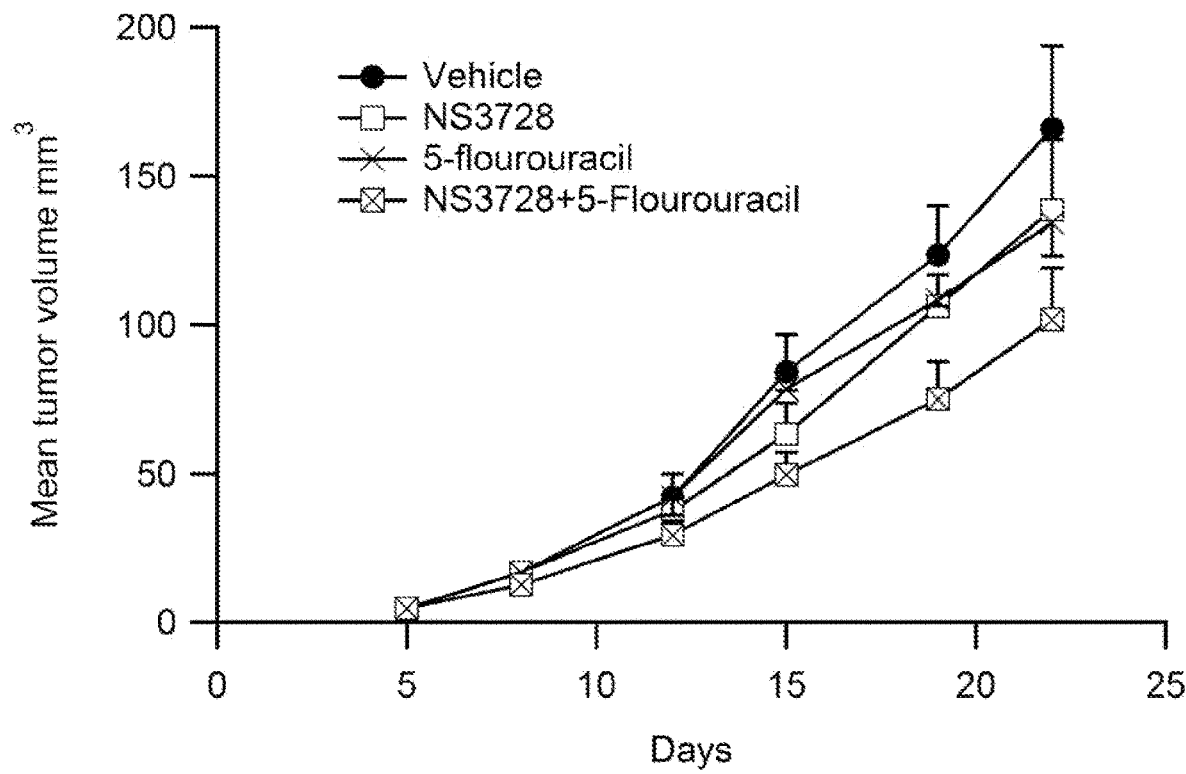
FIG. 3. Effect of NS3728 (80 mg/kg, PO), 5-flourouracil (30 mg/kg, IP) and the combination thereof on the growth of HT29 colon tumour xenografts compared to mice treated with vehicle in vivo.
Figure 4:
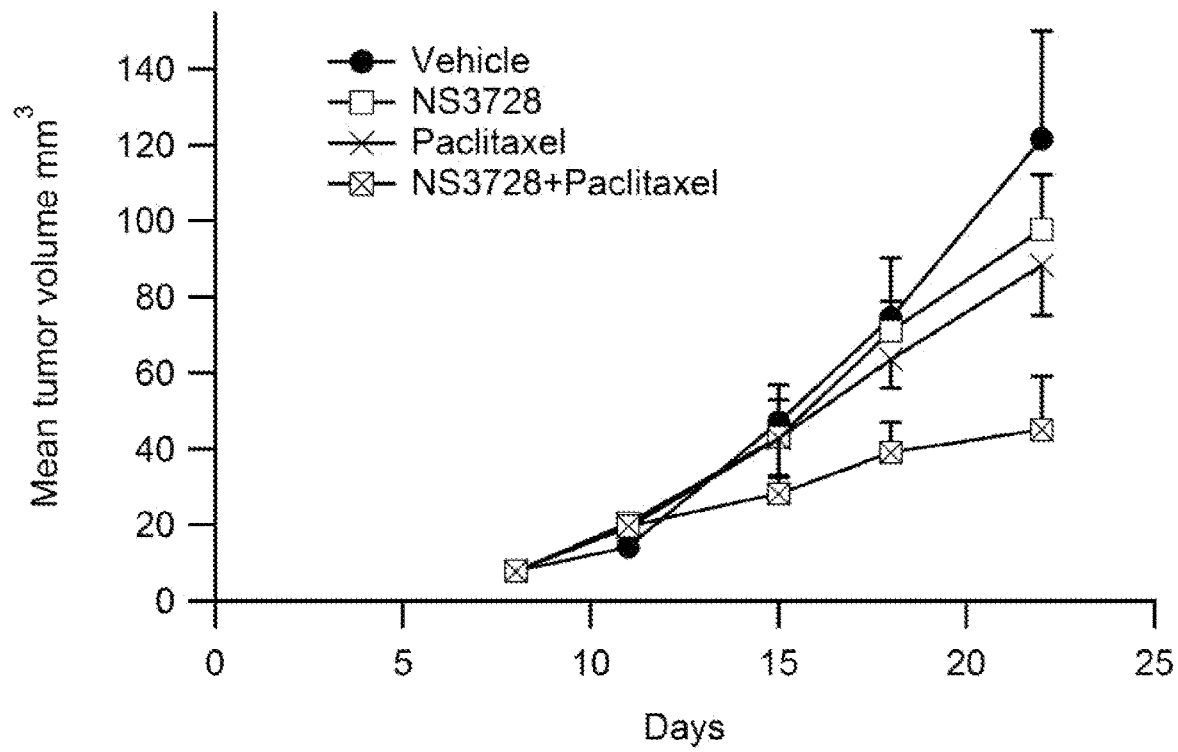
FIG. 4. Effect of NS3728 (80 mg/kg, PO), paclitaxel (5 mg/kg, IP) and the combination thereof on the growth of HT29 colon tumour xenografts compared to mice treated with vehicle in vivo.

The dosing occurred in periods (days 4-8; days 11-15, days 18-22) with daily dosing of both NS3728 and cytotoxic drug, interrupted by dosing holidays. The results are shown in FIG. 3 (5-flourouracil) and FIG. 4 (paclitaxel). In both experiments the tumour volume in the vehicle group increased in a superlinear way until a final tumour volume of 166 $mm^3$ in the 5-flourouracil experiment and 122 $mm^3$ in the paclitaxel experiment. A mild (non-significant) depression of the growth curves were observed with both NS3728 and cytotoxic drugs given as monotherapy. In contrast, the growth curves were further reduced with the combination therapy (NS3728 and the cytotoxic drug) with both cytotoxic drugs, respectively, reaching significance (t-test) to the control group for both combinations (P=0.03 for NS3728+5-flourouracil and P=0.003 for NS3728+paclitaxel).

In conclusion, we have demonstrated that a human xenografted HT29 tumour exhibits increased sensitivity to the combination treatment of NS3728 and either 5-flourourecil or paclitaxel as compared to monotherapy with one of the chemotherapeutic drugs. Thus, NS3728 is capable of potentiating the effect of 5-flourourecil and paclitaxel in vivo.

Example 3. Docetaxel and NS3728 in Docetaxel Resistant MCF-7 and MDA-MB231 Human Breast Cancer Cell Lines Breast cancer is a heterogenous disease and at least 6 subtypes of breast cancer have been described previously by Soerlie et al (PMID: 11553815). As a major difference, breast cancer can be divided into hormone (estrogen and progesterone) receptor positive and hormone receptor negative breast cancer. We have in our experiments included these two major subtypes. We established human breast cancer cell lines that are resistant to the chemotherapy docetaxel as described in Hansen et al 2015 (PMID: 25596703). These cell lines are MCF-7 and MDA-MB-231.

MCF-7: estrogen and progesterone receptor positive
MDA-MB-231: estrogen and progesterone receptor negative and HER2 receptor negative (the so-called triple negative phenotype)

We have examined the effects of NS3728 as single drug or in combination with docetaxel in docetaxel resistant breast cancer cell lines.

We employed standard MTT (3-(4,5-dimethylthiazol-2-yl)-2,5-diphenyltetrazolium bromide) cell viability assays. The cells were seeded in 96-well plates (10,000 cells/well) and allowed to adhere for 24 hours. Subsequently, NS3728, docetaxel or combinations of the two drugs were added for 72 hours before cell viability was determined. All values are expressed in percentage of untreated cells (named: "no treatment"). "DMSO" refers to the solvent control as both NS3728 and docetaxel are diluted in DMSO. Thus, the DMSO (Dimethyl sulfoxide) control is included to investigate any potential effect on cell viability by the organic solvent. Each data point was carried out in triplicate.

DMSO did not affect cell viability of the docetaxel resistant MCF-7 breast cancer cells. 65 nM of Docetaxel was chosen as this is the concentration to which the docetaxel resistant MCF-7 breast cancer cells were made resistant. 65 nM Docetaxel and 40 µM NS3728 provided as monotherapy did not decrease cell viability. The combination of 40 µM NS3728 and 65 nM Docetaxel resulted in a combinatory effect on cell viability for the docetaxel resistant MCF-7 breast cancer cells.

Figure 5:
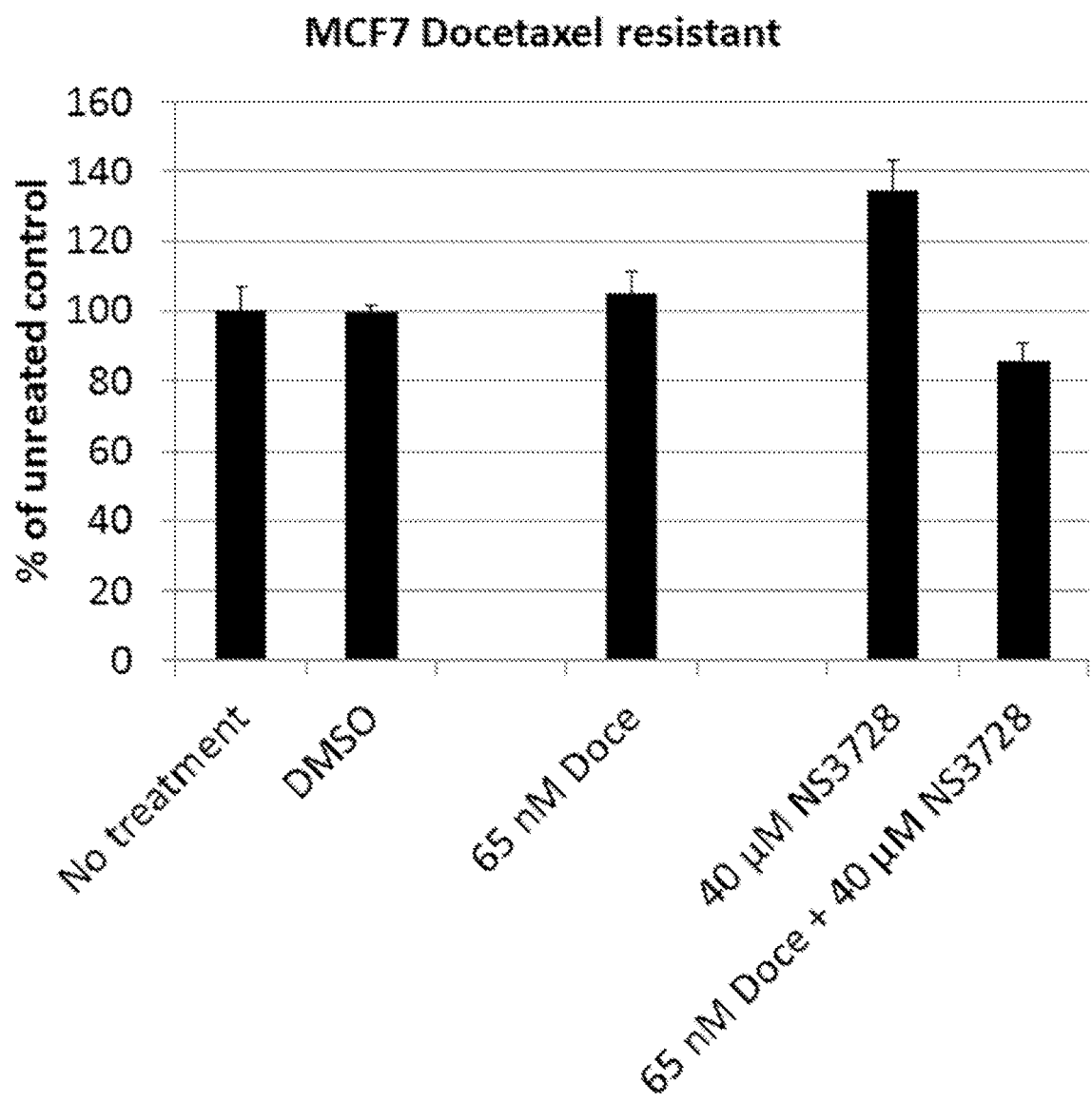
FIG. 5. Effect of NS3728, docetaxel and the combination thereof on cell viability of Docetaxel resistant MCF7 breast cancer cells in vitro. Error bars are standard deviations.

The effect of NS3728, docetaxel and the combination thereof on cell viability of Docetaxel resistant MCF-7 breast cancer cells is shown in FIG. 5.

DMSO did not affect cell viability of Docetaxel resistant MDA-MB-231 breast cancer cells. 150 nM of Docetaxel was chosen as this is the concentration to which the cells were made resistant. 150 nM Docetaxel reduced the viability to about 50% of untreated controls. 50 µM NS3728 did not decrease cell viability. At 50 µM NS3728 and 150 nM Docetaxel a combinatory effect on cell viability was observed for the Docetaxel resistant MDA-MB-231 breast cancer cells.

Figure 6:
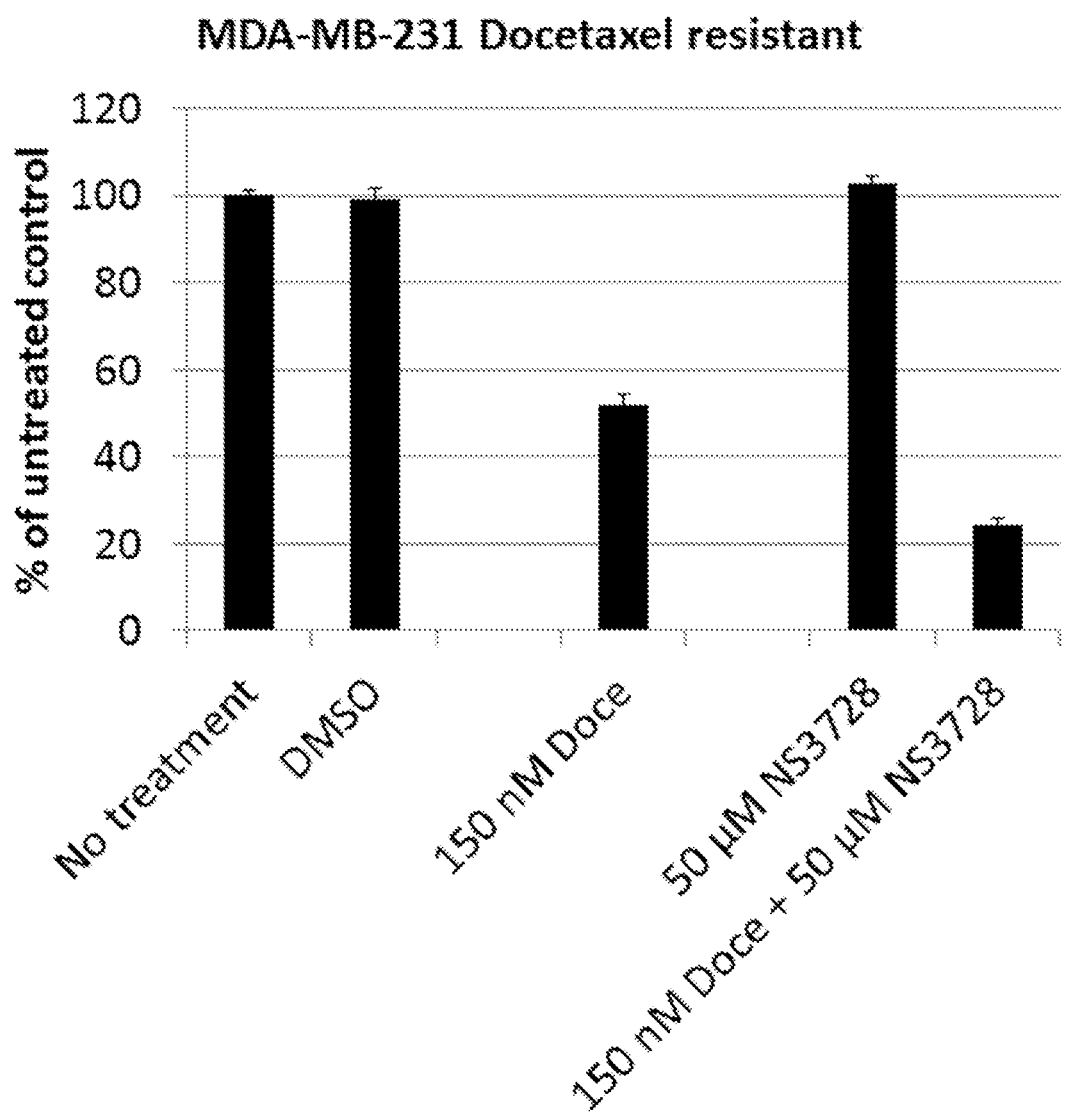
FIG. 6. Effect of NS3728, docetaxel and the combination thereof on cell viability of Docetaxel resistant MDA-MB-231 breast cancer cells in vitro. Error bars are standard deviations.

The effect of NS3728, docetaxel and the combination thereof on cell viability of Docetaxel resistant MDA-MB-231 breast cancer cells is shown in FIG. 6.

Conclusion

These preclinical studies demonstrate that the VRAC inhibitor NS3728 can enhance the effect of Docetaxel on Docetaxel resistant breast cancer cell lines. Thus, the data shows that NS3728 is capable of re-sensitising docetaxel-resistant cancer cells to treatment with Docetaxel.

Example 4. Oxaliplatin or SN38 and NS3728 in Parental HCT116, HT29 and LoVo Human Colorectal Cancer (CRC) Cell Lines CRC cells display genetic instability caused by chromosomal instability, microsatellite instability (MSI) and the CpG island methylator phenotype (CIMP), which result in activation of proto-oncogenes such as KRAS and inactivation of tumor suppressor genes such as TP53 (p53). The presence or absence of certain genetic alterations may determine the response of CRC patients to treatment and therefore it is important to study CRC cell lines that harbour different combinations of the genetic alterations described above. We have therefore chosen three cell lines to represent the major genetic alterations observed in CRC patients:

HCT116: MSI, KRAS mutated, TP53 wild type, CIMP+, CIN−, from primary tumor (Dukes C)
HT29: MSS, KRAS wild type, TP53 mutated, CIMP+, CIN+, from primary tumor (Dukes C)
LoVo: MSI, KRAS mutated, TP53 wild type, CIMP−, CIN−, from metastasis (Dukes C)

We have examined the effects of NS3728 as single drug or in combination with either OXP or SN-38 in the parental, i.e. drug-sensitive, cell lines. We have employed standard MTT (3-(4,5-dimethylthiazol-2-yl)-2,5-diphenyltetrazolium bromide) cell viability assays. The cells were seeded in 96-well plates (10,000 cells/well) and allowed to adhere for 24 hours. Subsequently, NS3728, OXP, SN-38 or combinations of NS3728 with one of the cytotoxic drugs were added for 48 hours before cell viability was determined. All values are expressed in percentage of untreated cells (named: "no treatment"). "DMSO" refers to the solvent control as both NS3728 and chemotherapeutic drugs are diluted in DMSO. Thus, the DMSO (Dimethyl sulfoxide) control is included to investigate any potential effect on cell viability by the organic solvent. Each data point was carried out in triplicate.

In parental cells, we have tested the effect of NS3728 as a single agent and in combination with either OXP or SN-38.

Parental CRC Cell Lines—NS3728 and OXP

DMSO caused a minor reduction in cell viability of HCT116 parental cells. NS3728 reduced cell viability to about 50% of untreated cells and OXP dose-dependently decreased cell viability of HCT116 parental cells. Combinations of 40 or 50 µM NS3728 and 0.16/0.8/4/20 µm Oxaliplatin did not inhibit cell viability more than either monotherapy in HCT116 parental cells.

Figure 7:
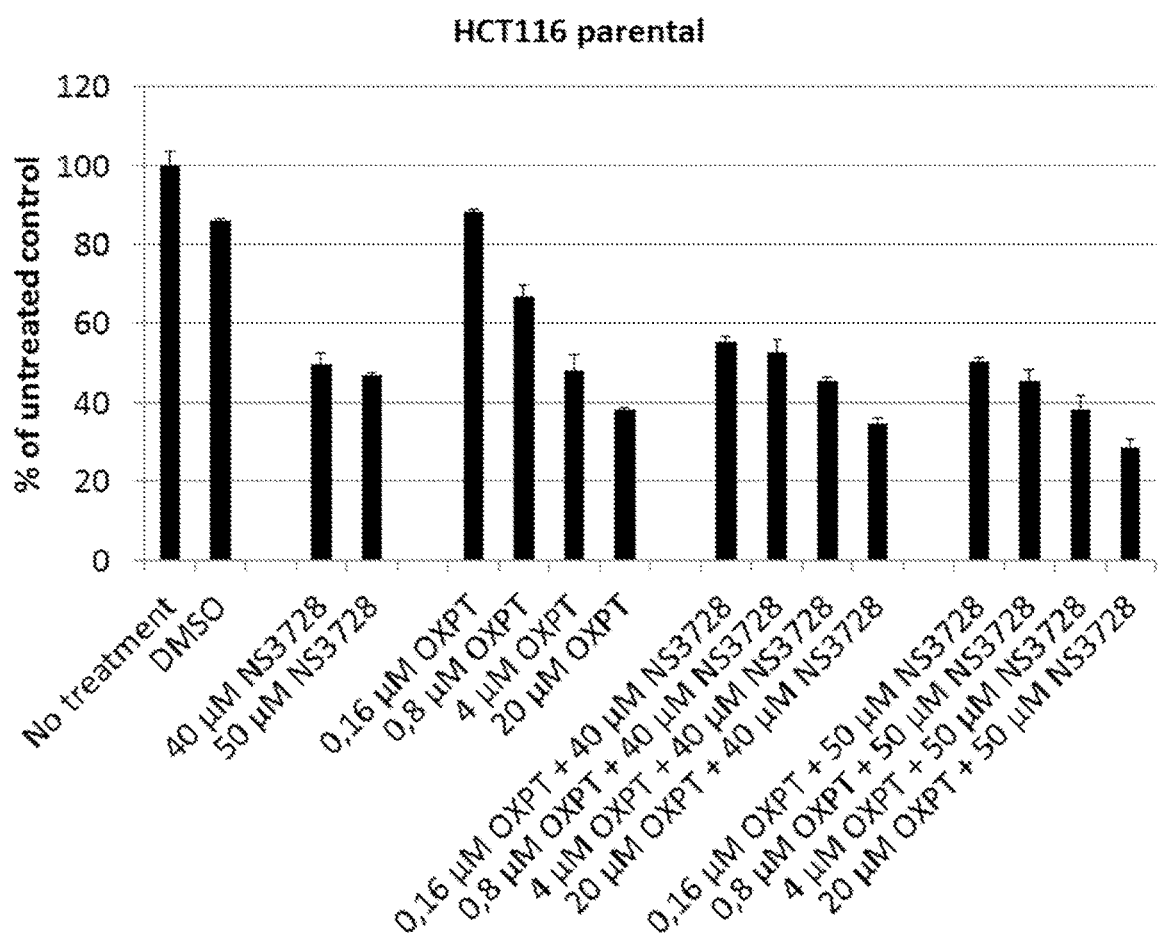
FIG. 7. Effect of NS3728, Oxalipatin and the combination thereof on cell viability of parental HCT116 CRC cancer cells in vitro. Error bars are standard deviations.

The effect of combination of NS3728 and OXA on cell viability of parental HCT116 CRC cancer cells is shown in FIG. 7.

In HT29 parental and LoVo parental cells we also did not observe any combinatorial inhibitory effect on cell viability of NS3728 and OXP (data not shown).

Thus, there does not seem to be any effect of combining NS3728 and oxaliplatin in OXP sensitive colorectal cancer.

HCT116 Parental CRC Cell Lines—NS3728 and SN-38

DMSO caused a minor reduction in cell viability. NS3728 reduced cell viability to about 50% of untreated cells at two concentrations (40 and 50 µM). SN-38 (0.16 µM) also decreased viability to about 50% of untreated cells. The combinations of 40 or 50 μM NS3728 and 0.16 μM SN-38 had a combinatorial inhibitory effect on cell viability with the 40 μM NS3728+SN-38 reducing cell viability to about 30% of untreated cells and the 50 μM NS3728+SN-38 reducing cell viability to about 23% of untreated cells.

Figure 8:
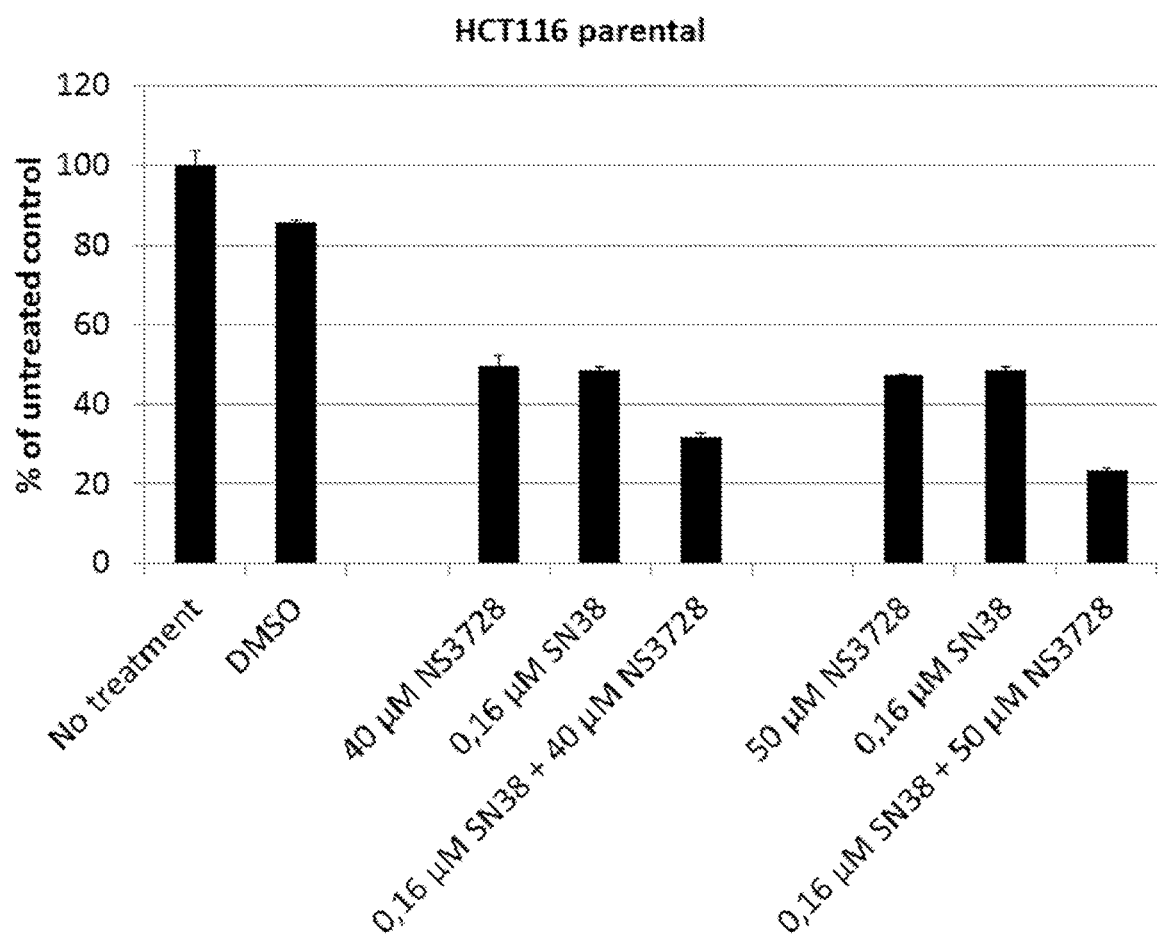
FIG. 8. Effect of NS3728, SN-38 and the combination thereof on cell viability of parental HCT116 CRC cancer cells in vitro. Error bars are standard deviations.

The effect of combination of NS3728 and SN-38 on cell viability of parental HCT116 CRC cancer cells is shown in FIG. 8.

HT29 Parental CRC Cell Lines—NS3728 and SN-38

DMSO reduced cell viability in this cell line to about 78% of untreated cells. NS3728 reduced cell viability to about 90% of untreated cells at 40 μM and to about 77% of untreated cells at 50 μM. SN-38 (0.032 μM) decreased viability to about 77% of untreated cells. Combinations of 40 or 50 μM NS3728 and 0.032 μM SN-38 caused a combinatorial inhibitory effect on cell viability with the 40 μM NS3728+SN-38 reducing cell viability to about 50% of untreated cells and the 50 μM NS3728+SN-38 reducing cell viability to about 38% of untreated cells.

Figure 9:
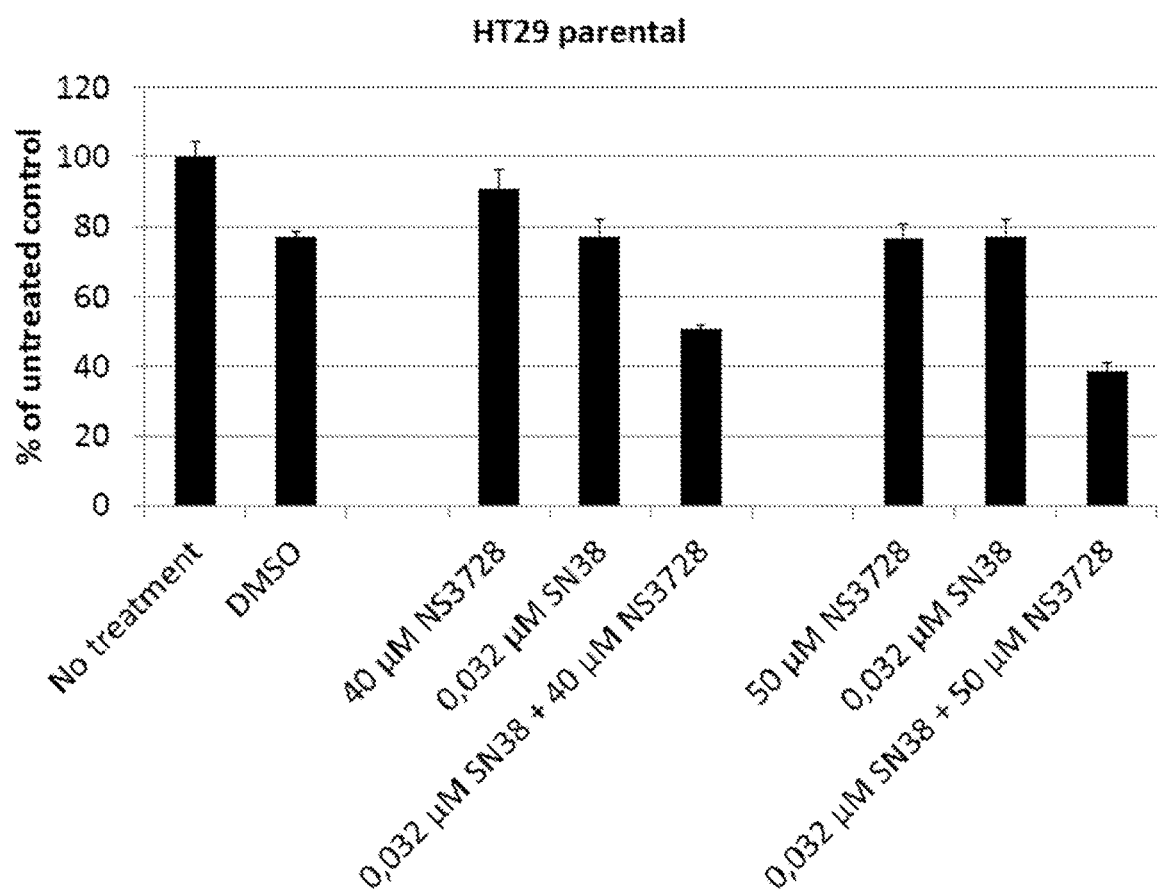
FIG. 9. Effect of NS3728, SN-38 and the combination thereof on cell viability of parental HT29 CRC cancer cells in vitro. Error bars are standard deviations.

The effect of combination of NS3728 and SN-38 on cell viability of parental HT29 CRC cancer cells is shown in FIG. 9.

LoVo Parental CRC Cell Lines—NS3728 and SN-38

DMSO reduced cell viability in this cell line to about 75% of untreated cells. NS3728 reduced cell viability to about 45% of untreated cells at 40 μM and to about 38% of untreated cells at 50 μM. SN-38 (0.0064 μM) decreased viability to about 53% of untreated cells. Combinations of 40 or 50 μM NS3728 and 0.0064 μM SN-38 caused a combinatorial inhibitory effect on cell viability with the 40 μM NS3728+SN-38 reducing cell viability to about 35% of untreated cells and the 50 μM NS3728+SN-38 reducing cell viability to about 22% of untreated cells.

Figure 10:
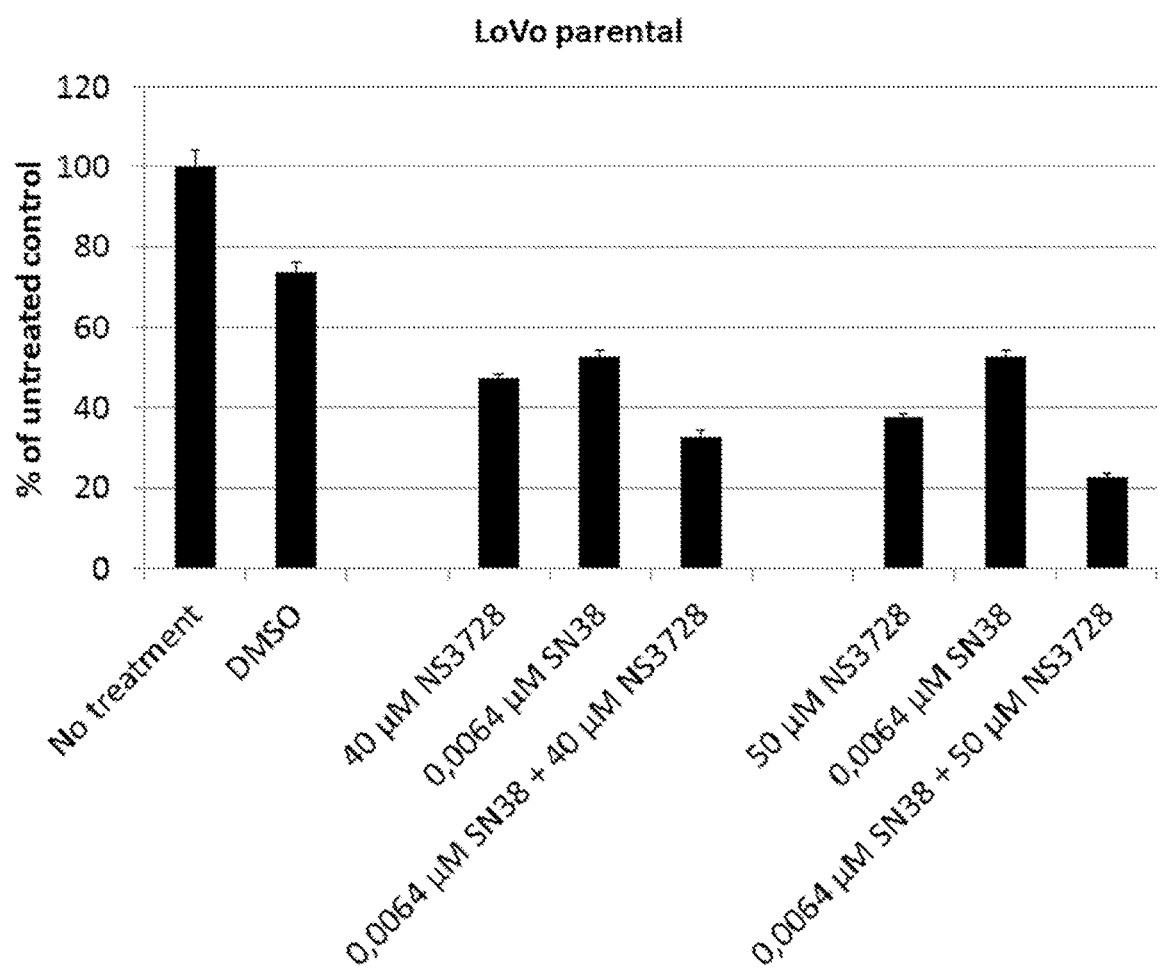
FIG. 10. Effect of NS3728, SN-38 and the combination thereof on cell viability of parental LoVo CRC cancer cells in vitro. Error bars are standard deviations.

The effect of combination of NS3728 and SN-38 on cell viability of parental LoVo CRC cancer cells is shown in FIG. 10.

Conclusion

These preclinical studies demonstrate that the VRAC inhibitor NS3728 can 1) inhibit CRC cell growth when administered as monotherapy and 2) enhance the effect of certain types of chemotherapy on human CRC cells. No combinatory effect of NS3728 and oxaliplatin was found. Thus, the results show that treatment with a VRAC inhibitor can potentiate the effect of certain types of chemotherapy.

Example 5. Oxaliplatin or SN-38 and NS3728 in Oxaliplatin (OXP) or SN-38 Resistant HCT116, HT29 and LoVo Human Colorectal Cancer (CRC) Cell Lines We have established human CRC cancer cell lines that are resistant to the chemotherapeutics oxaliplatin (OXP) or SN-38 (the active metabolite of irinotecan) as described in Jensen et al 2015 (PMID: 25759163). These cell lines are HCT116, HT29 and LoVo.

We have examined the effects of NS3728 as single drug or in combination with either OXP or SN-38 in the OXP and SN-38 resistant cell lines. We have employed standard MTT (3-(4,5-dimethylthiazol-2-yl)-2,5-diphenyltetrazolium bromide) cell viability assays. The cells were seeded in 96-well plates (10,000 cells/well) and allowed to adhere for 24 hours. Subsequently, NS3728, OXP, SN-38 or combinations of the drugs were added for 48 hours before cell viability was determined. All values are expressed in percentage of untreated cells (named: "no treatment"). "DMSO" refers to the solvent control as both NS3728 and chemotherapeutic drugs are diluted in DMSO. Thus, the DMSO (Dimethyl sulfoxide) control is included to investigate any potential effect on cell viability by the organic solvent. Each data point was carried out in triplicate.

In OXP resistant cells, we have tested the effect of NS3728 as a single agent and in combination with either SN-38 or OXP.

In SN-38 resistant cells, we have tested the effect of NS3728 as a single agent and in combination with either SN-38 or OXP.

SN-38 Resistant CRC Cell Lines—NS3728 and Oxaliplatin

No effect of combining NS3728 and Oxaliplatin was found in the SN-38 resistant HCT116, HT29 and LoVo CRC cancer cell lines as compared to monotherapy with either NS3728 or Oxaliplatin (Data not shown). Thus, NS3728 does not seem to be capable of potentiating the therapeutic effect of oxaliplatin in oxaliplatin sensitive CRC cells which are resistant to SN-38.

HCT116 SN-38 Resistant CRC Cell Lines—NS3728 and SN-38

In this cell line DMSO had no effect on cell viability. NS3728 (30 μM) reduced cell viability to about 85% of untreated cells and SN-38 (4 μM) had almost no effect on cell viability. However, combinations of 4 μM SN-38 and 30 μM NS3728 caused a combined reduction in cell viability and thus significantly reduced cell viability to about 60%.

Figure 11:
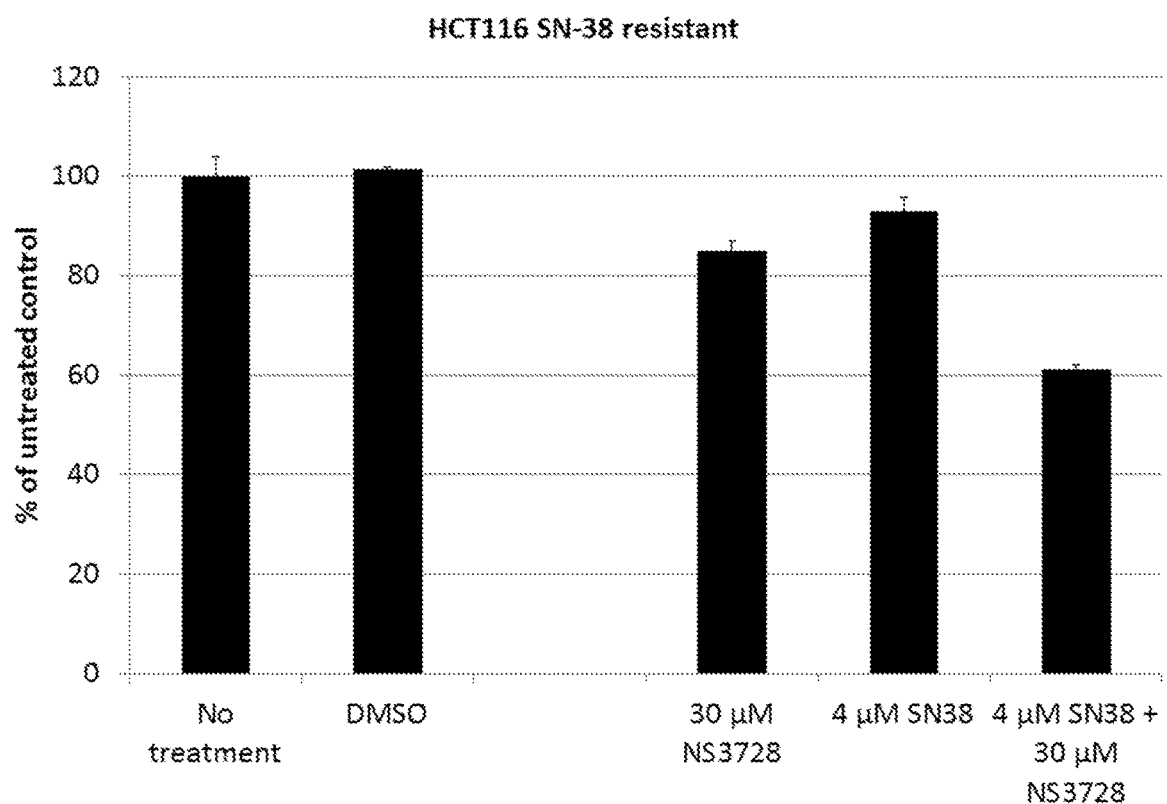
FIG. 11. Effect of NS3728, SN-38 and the combination thereof on cell viability of SN-38 resistant HCT116 CRC cancer cells in vitro. Error bars are standard deviations.

The effect of combination of NS3728 and SN-38 on cell viability of SN-38 resistant HCT116 CRC cancer cells is shown in FIG. 11.

HT29 SN-38 Resistant CRC Cell Lines—NS3728 and SN-38

DMSO had no effect on cell viability. NS3728 (30 μM) increased viability to about 120% of untreated cells. NS3728 (40 μM) had no effect on cell viability and NS3728 (50 μM) reduced viability to about 85% of untreated cells. SN-38 (0.8 μM) reduced viability to about 78% of untreated cells. Combinations of 0.8 μM SN-38 and 30/40/50 μM NS3728 caused a significant combined reduction in cell viability to less than 30% of untreated cells for all three NS3728 concentrations.

Figure 12:
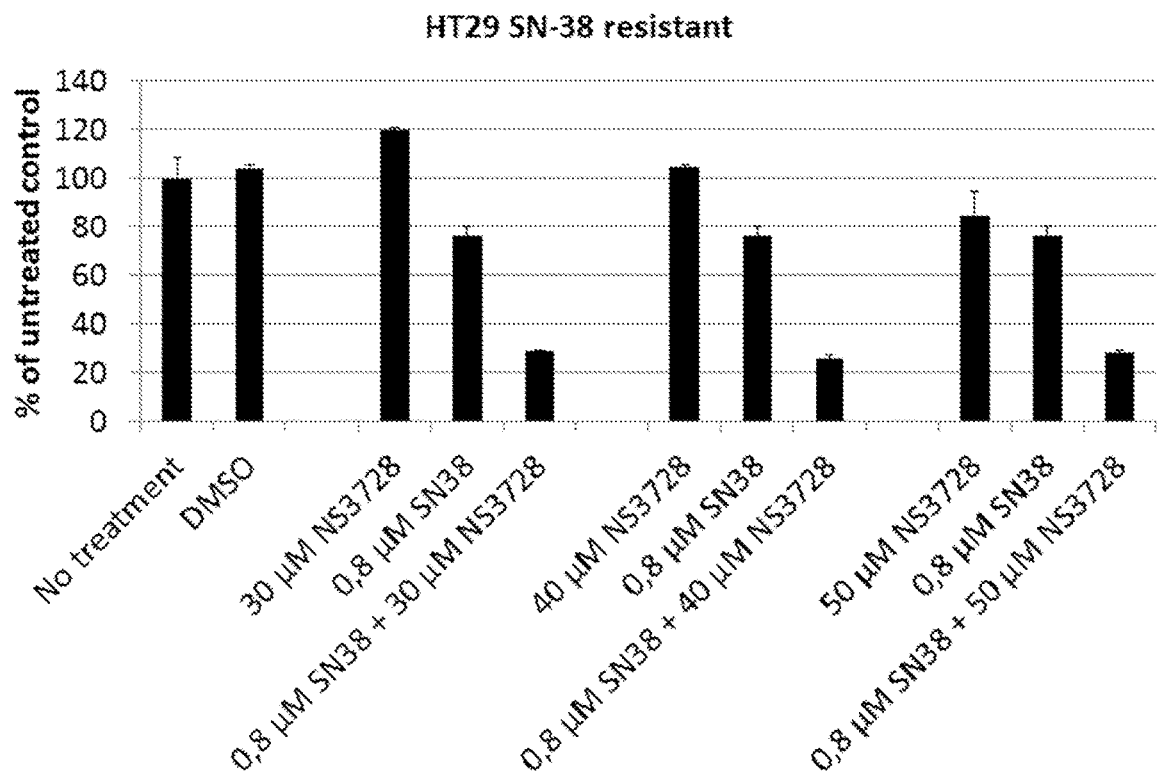
FIG. 12. Effect of NS3728, SN-38 and the combination thereof on cell viability of SN-38 resistant HT29 CRC cancer cells in vitro. Error bars are standard deviations.

The effect of combination of NS3728 and SN-38 on cell viability of SN-38 resistant HT29 CRC cancer cells is shown in FIG. 12.

LoVo SN-38 Resistant CRC Cancer Cells—NS3728 and SN-38

DMSO reduced cell viability in this cell line to about 80% of untreated cells. NS3728 (30 μM) reduced viability to about 80% of untreated cells, NS3728 (40 μM) reduced viability to about 57% and NS3728 (50 μM) reduced viability to about 50% of untreated cells. SN-38 (0.16 μM) reduced viability to about 78% of untreated cells. Combinations of 0.16 μM SN-38 and 30/40/50 μM NS3728 caused a significant combined reduction in cell viability to less than 20% of untreated cells for all three NS3728 concentrations.

Figure 13:
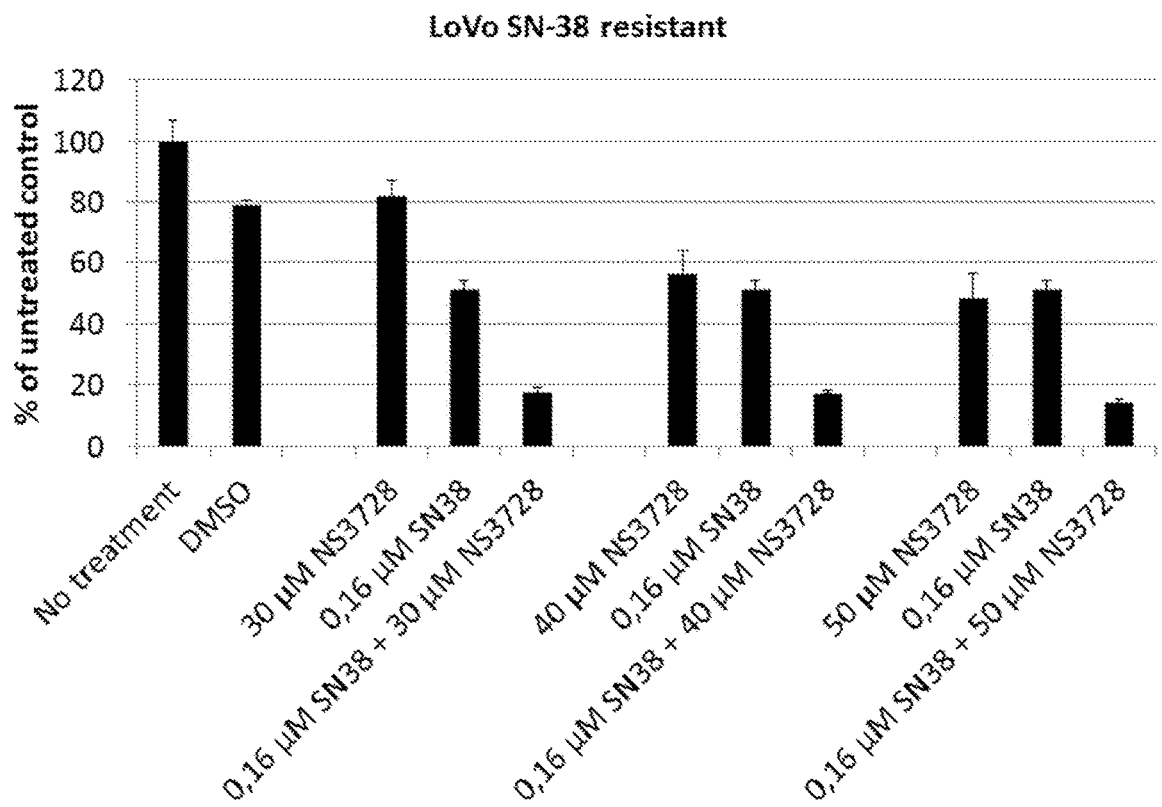
FIG. 13. Effect of NS3728, SN-38 and the combination thereof on cell viability of SN-38 resistant LoVo CRC cancer cells in vitro. Error bars are standard deviations.

The effect of combination of NS3728 and SN-38 on cell viability of SN-38 resistant LoVo CRC cancer cells is shown in FIG. 13.

HT29 Oxaliplatin Resistant CRC Cancer Cells—NS3728 and SN-38

DMSO caused essentially no change in cell viability. NS3728 (20 μM) reduced viability to about 85% of untreated cells and SN-38 (0.1 μM) reduced viability to about 43% of untreated cells. Combinations of 20 μM NS3728 and 0.1 μM SN-38 caused a combined effects on cell viability.

Figure 14:
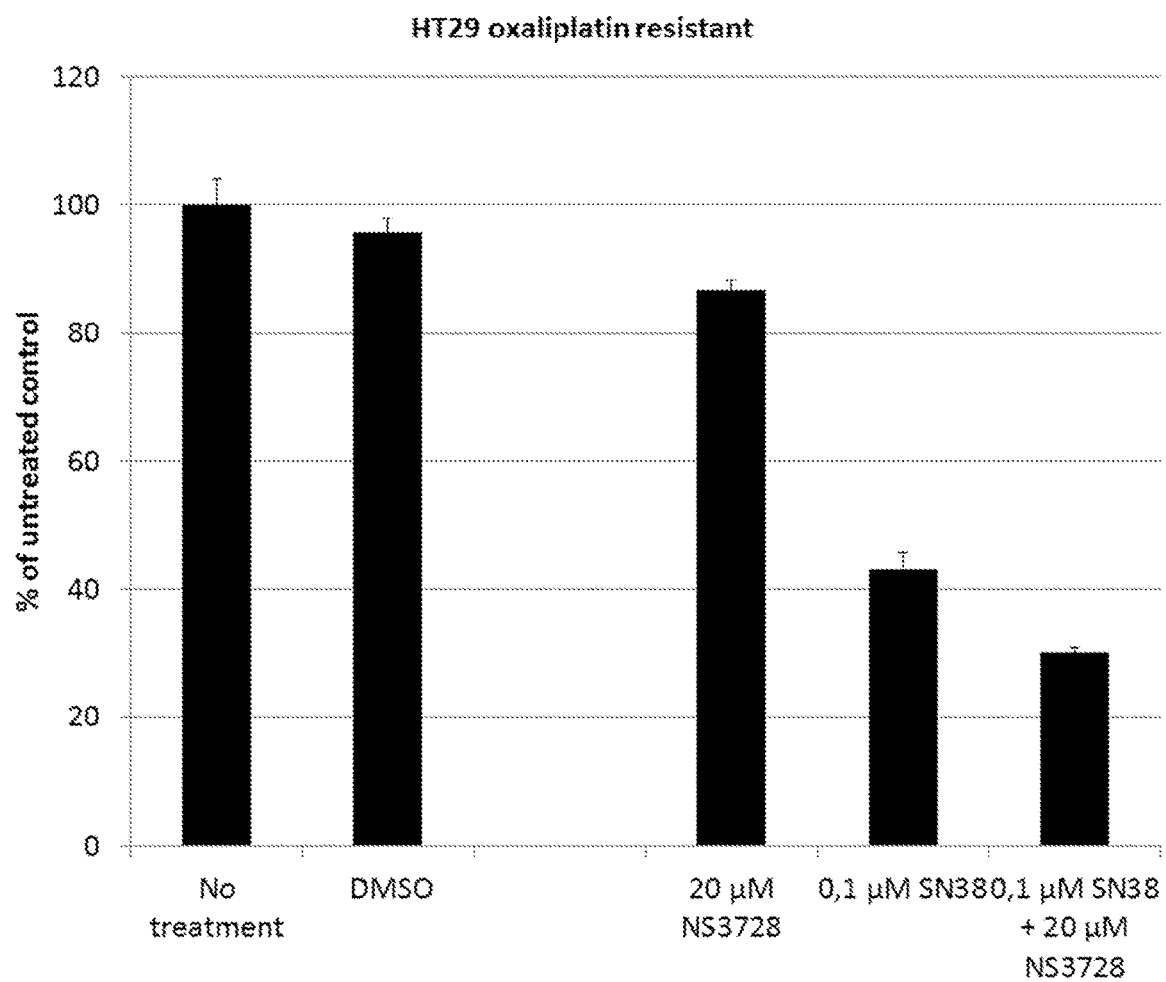
FIG. 14. Effect of NS3728, SN-38 and the combination thereof on cell viability of oxaliplatin resistant HT29 CRC cancer cells in vitro. Error bars are standard deviations.

The effect of combination of NS3728 and SN-38 on cell viability of oxaliplatin resistant HT29 CRC cancer cells is shown in FIG. 14.

LoVo Oxaliplatin Resistant CRC Cancer Cells—NS3728 and SN-38

DMSO reduced viability to about 85% of untreated cells. Combinations of 20/30/40/50 μM NS3728 and SN-38 (0.005 μM) all had significant combined effects on cell viability.

Figure 15:
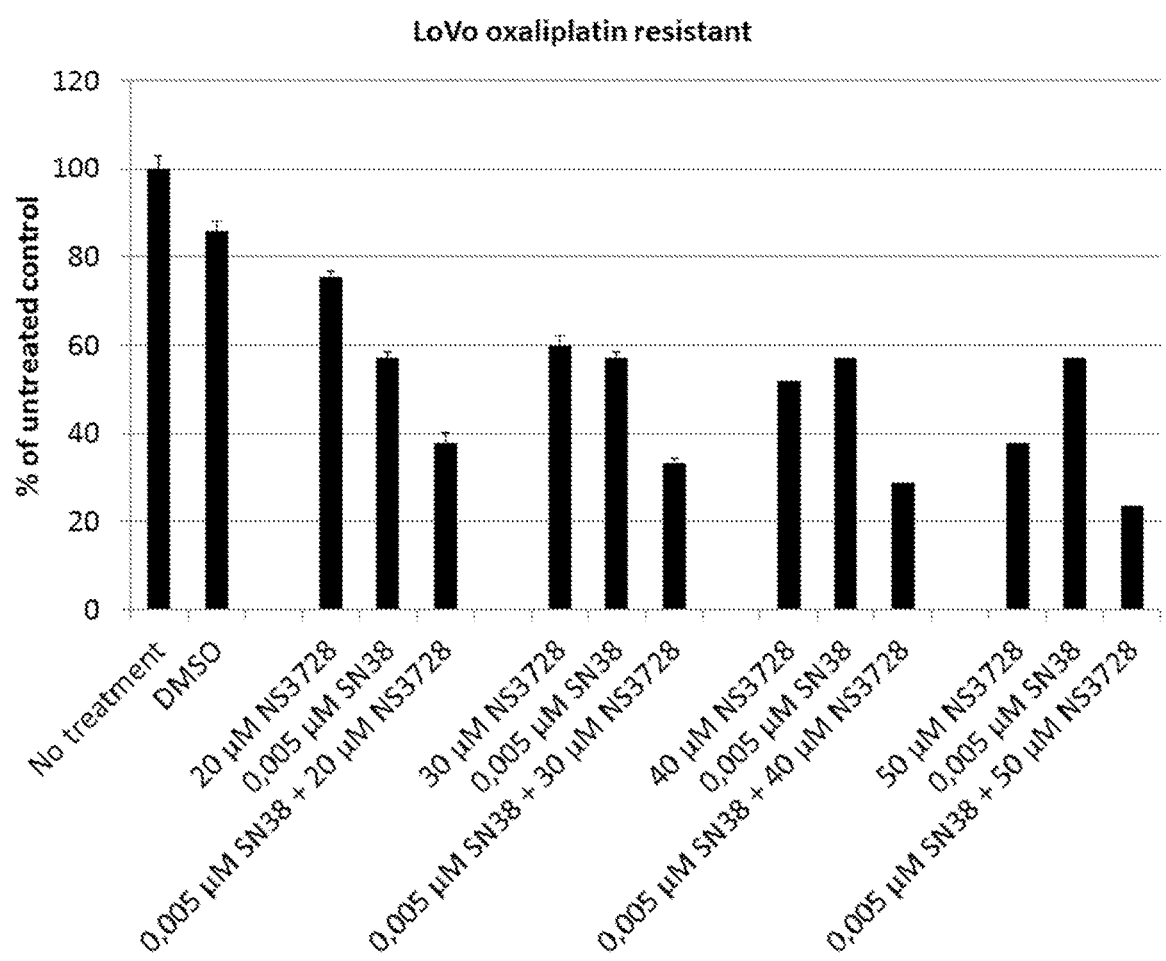
FIG. 15. Effect of NS3728, SN-38 and the combination thereof on cell viability of oxaliplatin resistant LoVo CRC cancer cells in vitro. Error bars are standard deviations.

The effect of combination of NS3728 and SN-38 on cell viability of oxaliplatin resistant LoVo CRC cancer cells is shown in FIG. 15.

HT116 Oxaliplatin Resistant CRC Cancer Cells—NS3728 and SN-38

In oxaliplatin resistant HCT116 CRC cells a minor inhibitory combined effect was observed when NS38728 was combined with SN-38 (data not shown).

Oxaliplatin Resistant CRC Cancer Cells—NS3728 and Oxaliplatin

No effect of combining NS3728 and Oxaliplatin was found in the oxaliplatin resistant HCT116, HT29 and LoVo CRC cancer cell lines as compared to monotherapy with either NS3728 or Oxaliplatin (Data not shown). Thus, NS3728 does not seem to be capable of re-sensitising Oxaliplatin resistant CRC cells to treatment with oxaliplatin.

Conclusion

These preclinical studies demonstrate that the VRAC inhibitor NS3728 can enhance the effect of certain types of chemotherapy on resistant CRC cell lines. Of particular interest is that NS3728 also enhanced the effect of SN-38 in cancer cells with acquired SN-38 resistance or with acquired oxaliplatin resistance. The data suggests that NS3728 is capable of re-sensitising SN-38 drug-resistant cancer cells to treatment with SN-38.

Example 6. Tamoxifen or Fulvestrant in Combination with NS3728 in Tamoxifen Resistant MCF-7/LCC2 or Fulvestrant MCF-7/LCC9 Human Breast Cancer Cell Lines We established human breast cancer cell lines that are resistant to the anti-estrogen Tamoxifen as described in Brünner et al 1993 (PMID: 8324732). These cell lines are MCF-7/LCC2. We also established human breast cancer cell lines that are resistant to the anti-estrogen Fulvestrant as described in Brünner et al 1997 (PMID: 9270017). MCF-7 is an estrogen and progesterone receptor positive cell line.

We have examined the effects of NS3728 as single drug or in combination with either Tamoxifen or Fulvestrant in MCF-7/LCC2 or MCF-7/LCC9) drug-resistant breast cancer cell lines, respectively.

We employed standard MTT (3-(4,5-dimethylthiazol-2-yl)-2,5-diphenyltetrazolium bromide) cell viability assays. The cells were seeded in 96-well plates (10,000 cells/well) and allowed to adhere for 24 hours. Subsequently, NS3728, docetaxel or combinations of the two drugs were added for 72 hours before cell viability was determined. All values are expressed in percentage of untreated cells (named: "no treatment"). Each data point was carried out in triplicate.

Figure 16:
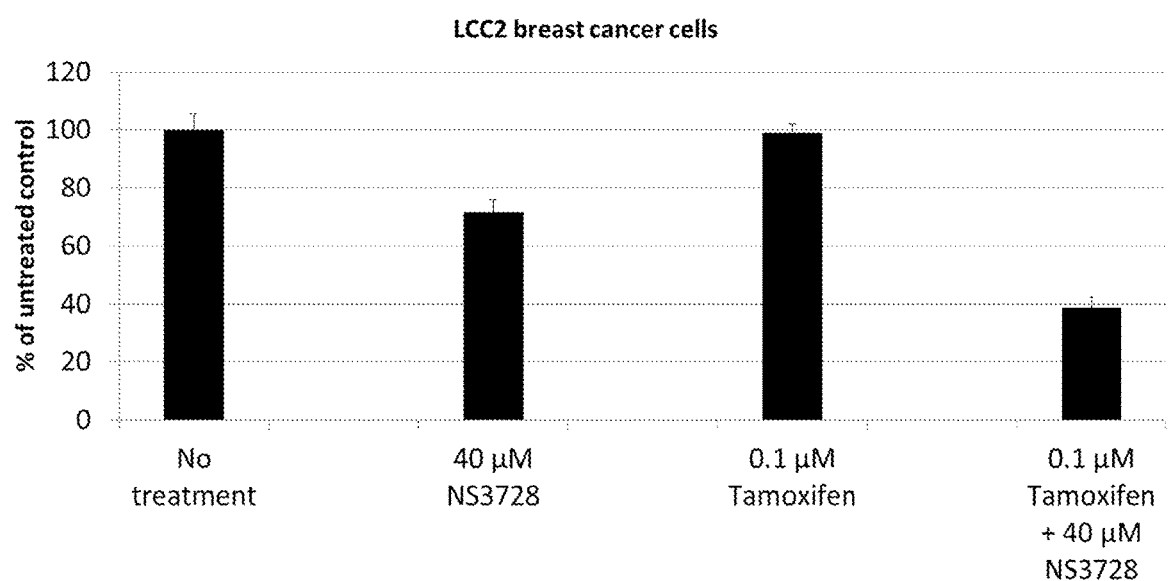
FIG. 16. Effect of NS3728, tamoxifen and the combination thereof on cell viability of tamoxifen resistant MCF7/LCC2 breast cancer cells in vitro. Error bars are standard deviations.

0.1 µM of Tamoxifen was chosen as this is the concentration which was shown in the original publication to cause only minor cell growth effects on MCF-7/LCC2 cells whereas growth of Tamoxifen sensitive cells were significantly more inhibited. 40 µM NS3728 caused a minor reduction in cell viability to 70% of untreated control. 0.1 µM Tamoxifen had no effect on the cell viability of the tamoxifen-resistant MCF-7/LCC2 cells. The combination of 40 µM NS3728 and 0.1 µM Tamoxifen caused a strong and significant ($P<0.05$) reduction of MCF-7/LCC2 cell viability to less than 40% of untreated cells (FIG. 16).

Figure 17:
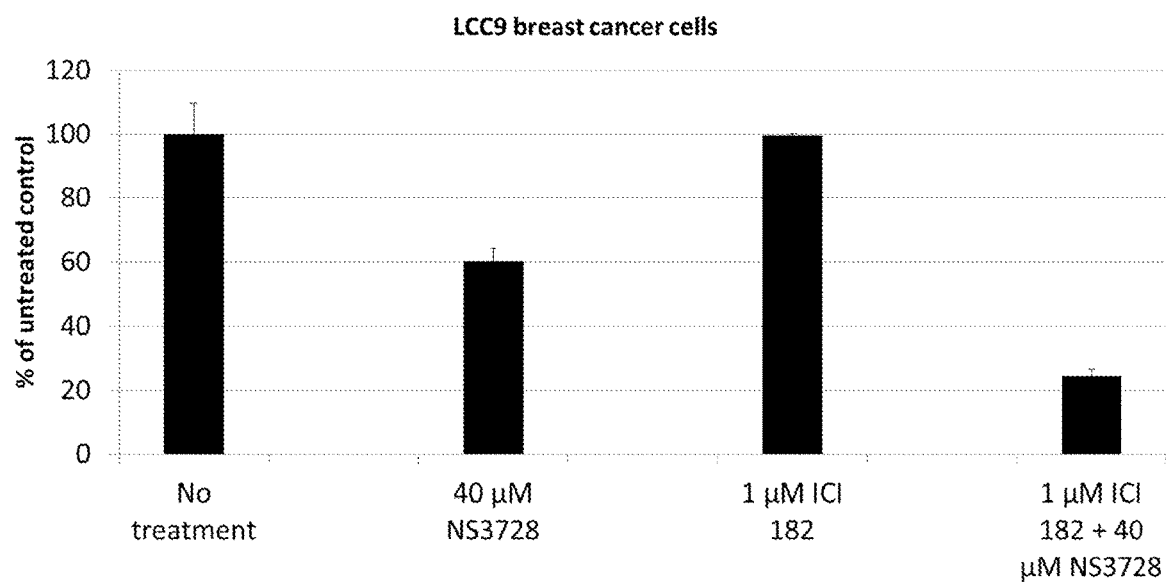
FIG. 17. Effect of NS3728, ICI182,780 (Fulvestrant/Faslodex) and the combination thereof on cell viability of ICI182,780 resistant MCF7/LCC9 breast cancer cells in vitro. Error bars are standard deviations.

1 µM of Fulvestrant was chosen as this is the concentration that was applied in the original publication as the final concentration to establish the MCF-7/LCC9 cell line and this concentration is strongly inhibiting growth of Fulvestrant sensitive MCF-7 cells (Brunner et al, 1997, PMID 9270017). 40 µM NS3728 caused a reduction in cell viability to 60% of untreated control. 1 µM Fulvestrant had no effect on the cell viability of the fulvestrant-resistant MCF-7/LCC9 cells. The combination of 40 µM NS3728 and 1 µM Fulvestrant caused a strong and significant ($P<0.05$) reduction of MCF-7/LCC9 cell viability to 24% of untreated cells (FIG. 17).

Conclusion

These preclinical studies demonstrate that the VRAC inhibitor NS3728 can enhance the effect of two types of anti-estrogens, namely Tamoxifen and Fulvestrant, on MCF-7 breast cancer cells that are made resistant to these types of anti-estrogens. Thus, the data suggest that NS3728 is capable of re-sensitising anti-estrogen-resistant breast cancer cells to treatment with anti-estrogens, in particular to tamoxifen and fulvestrant.

Example 7. In Vivo Investigation of the Re-Sensitizing Effect of NS3728 in Docetaxel-Resistant Xenograft Tumors (Breast Cancer)

Mouse xenograft experiments are performed with a pair of sensitive- and docetaxel-resistant triple-negative human breast cancer cell lines (MDA-MB-231). The mice used for the experiments are severely immunocompromised to prevent rejection of the human cancer cells.

The experimental set-up comprises three stages:
1. "growth"
2. "dose-response"
3. "drug treatment"

Stage 1: Growth of Sensitive (Parental) and Docetaxel-Resistant MDA-MB-231 Cells To determine the optimal cell number for xenograft tumor growth of docetaxel-sensitive and docetaxel-resistant MDA-MB-231 cells, two groups of mice are inoculated with different numbers of the sensitive or the docetaxel-resistant MDA-MB-231 cells. This experiment determines the optimal number of cancer cells which is important for the subsequent dose-response experiments in Stages 2 and 3.

Stage 2: Resistance Phenotype, Dose-Response of Docetaxel

To confirm the docetaxel-sensitive and -resistant phenotypes in the xenografted MDA-MB-231 cells, the mice are treated with docetaxel when tumors have established. Sensitive or docetaxel-resistant MDA-MB-231 cells are inoculated into mice, with cell numbers as determined from Stage 1. This experiment is important to demonstrate that cancer cells are also sensitive or resistant, respectively, in an in vivo setting.

Stage 3: Docetaxel Re-Sensitizing Treatment with NS3728

To determine the re-sensitizing effect of NS3728 in combination with docetaxel in docetaxel-resistant xenograft tumors, parental and docetaxel-resistant MDA-MB-231 cells are inoculated into mice and treated with vehicle (control group), docetaxel alone, NS3728 alone or a combination of NS3728 and docetaxel.

In all steps, tumor formation is monitored by palpation and measured by caliper. Tumor volume is calculated and is plotted against time in a growth-curve. The mice are euthanized when the tumors are near maximal size (12 mm) or if the mice display any signs of discomfort or illness.

Conclusion

Based on our in vitro experiments (FIG. 6) and the xenograft experiments with paclitaxel (FIG. 4) we expect to observe that a combination of docetaxel and NS3728 will restore docetaxel sensitivity in the xenografted docetaxel resistant MDA-MB-231 cells, reflected in reduced tumor volume in comparison to either NS3728 alone or docetaxel alone.

The invention claimed is:

1. A method of sensitizing cancer cells of a cancer to an anti-cancer agent or potentiating the therapeutic effect of an anti-cancer agent comprising administering to a subject in need thereof an effective amount of a VRAC modulator and an effective amount of an anti-cancer agent; wherein the cancer is selected from the group consisting of: colorectal cancer, breast cancer, lung cancer (non small cell lung cancer and small cell lung cancer), glioblastomas, head and neck cancers, malignant melanomas, basal cell skin cancer, squamous cell skin cancer, liver cancer, pancreatic cancer, prostate cancer, anal cancer, cervix uteri cancer, bladder cancer, corpus uteri cancer, ovarian cancer, gall bladder cancer, sarcomas, leukemias (myeloid and lymphatic), lymphomas, and myelomatosis.

2. The method according to claim 1, wherein the VRAC modulator is:
   a) co-administered with the anti-cancer agent;
   b) administered prior to administering the anti-cancer agent; or
   c) administered after administering the anti-cancer agent.

3. The method according to claim 1, wherein the anti-cancer agent is a chemotherapeutic agent selected from the group consisting of topoisomerase inhibitors, anti-hormone agents, alkylating agents, mitotic inhibitors, antimetabolites, anti-tumour antibiotics, corticosteroids, targeted anti-cancer therapy, differentiating agents and immunotherapy.

4. The method according to claim 1, wherein the anti-cancer agent is a topoisomerase I inhibitor.

5. The method according to claim 1 wherein the anti-cancer agent is an anti-hormone agent, and the cancer is a steroid-hormone receptor positive cancer.

6. The method according to claim 3, wherein the anti-hormone agent is an anti-estrogen or an anti-progestogen.

7. The method according to claim 1, wherein the anti-cancer agent is:
   a) an alkylating agent;
   b) a mitotic inhibitor; or
   c) an antimetabolite.

8. The method according to claim 1, wherein the VRAC modulator is a compound of general formula I

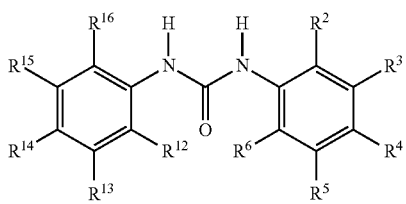

or a pharmaceutically acceptable salt thereof
wherein $R^2$ represents tetrazolyl; and
$R^3$, $R^4$, $R^5$, $R^6$, $R^{12}$, $R^{13}$, $R^{14}$, $R^{15}$, and $R^{16}$ independently of each other represent hydrogen, halo, trifluoromethyl, nitro, alkyl, alkylcarbonyl, —NR$^a$R$^b$, —NR$^a$—CO—R$^b$, phenyl or heteroaryl;
which phenyl is optionally substituted with halo, trifluoromethyl, nitro, —CO—NHR$^c$, —CO—O—R$^c$ or —CO—NR'R'';
wherein R$^c$ is hydrogen, alkyl, or phenyl;
R' and R'' independently of each other are hydrogen or alkyl; or
R' and R'' together with the nitrogen to which they are attached form a 5- to 7-membered heterocyclic ring, which ring may optionally comprise as a ring member, one oxygen atom, and/or one additional nitrogen atom, and/or one carbon-carbon double bond, and/or one carbon-nitrogen double bond;
and which heterocyclic ring may optionally be substituted with alkyl;
R$^a$ and R$^b$ independently of each other are hydrogen or alkyl; or
$R^{15}$ and $R^{16}$, or $R^{14}$ and $R^{15}$ together with the phenyl ring to which they are attached form a naphthyl ring or an indanyl ring; and $R^3$, $R^4$, $R^5$, $R^6$, $R^{12}$ and $R^{13}$ and the remaining one of $R^{14}$, $R^{15}$ and $R^{16}$ are as defined above.

9. The method of claim 8, wherein
$R^3$, $R^5$, and $R^6$ represent hydrogen; and
$R^4$ represents:
   a) halo; or
   b) phenyl substituted with trifluoromethyl, nitro or —CO—NHR$^c$;
wherein R$^c$ is phenyl.

10. The method of claim 8, wherein the compound is
N-4-Nitrophenyl-N'-[4-bromo-2-(1-H-tetrazol-5-yl)phenyl] urea;
N-3,5-Di(trifluoromethyl)phenyl-N'-[4-bromo-2-(1-H-tetrazol-5-yl)phenyl] urea;
N-3-Trifluoromethylphenyl-N'-[4-(3-nitrophenyl)-2-(1-H-tetrazol-5-yl)phenyl] urea;
N-3-Trifluoromethylphenyl-N'-[4-(4-anilinocarbonylphenyl)-2-(1-H-tetrazol-5-yl)phenyl] urea;
N-3-Trifluoromethylphenyl-N'-[4-(4-trifluoromethylphenyl)-2-(1-H-tetrazol-5-yl)phenyl] urea;
N-(3-Trifluoromethyl-phenyl)-N'-[2-(1-H-tetrazol-5-yl)-phenyl] urea;
N-(3-Trifluoromethyl-phenyl)-N'-[4-bromo-2-(1-H-terazol-5-yl)-phenyl] urea;
N-(3-Trilfuoromethyl-phenyl)-N'-[4-phenyl-2-(1-H-tetrazol-5-yl)-phenyl] urea;
N-(3-Chloro-phenyl)-N'-[2-(1-H-tetrazol-5-yl)-phenyl] urea;
N-(3-Trifluoromethyl-phenyl)-N'-[4-amino-2-(1-H-tetrazol-5-yl)-phenyl] urea;
N-(3-Trifluoromethyl-phenyl)-N'-[4-acetylamino-2-(1-H-tetrazol-5-yl)-phenyl] urea;
N-(3-Trilfuoromethyl-phenyl)-N'-[4-carbamoyl-2-(1-H-tetrazol-5-yl)-phenyl] urea;
N-(3-Trifluoromethyl-phenyl)-N'-[4-(N'',N''-dimethyl-carbamoyl)-2-(1-H-tetrazol-5-yl)-phenyl] urea;
3'-(1-H-tetrazol-5-yl)-4'-[3-(3-trifluoromethyl-phenyl)-ureido]-biphenyl-4-carboxylic acid;
N-(Indan-5-yl)-N'-[2-(1-H-tetrazol-5-yl)-phenyl] urea;
N-(Biphenyl-4-yl)-N'-[2-(1-H-tetrazol-5-yl)-phenyl] urea;
N-(Biphenyl-3-yl)-N'-[2-(1-H-tetrazol-5-yl)-phenyl] urea;
N-(3-Acetyl-phenyl)-N'-[2-(1-H-tetrazol-5-yl)-phenyl] urea;
N-(Biphenyl-3-yl)-N'-[2-(1-H-tetrazol-5-yl)-phenyl] urea;
N-[3-(Pyridin-3-yl)-phenyl]-N'-[2-(1-H-tetrazol-5-yl)-phenyl] urea;
N-(3-Bromo-phenyl)-N'-[4''-(4-methyl-piperazine-1-carbonyl)-3-(1-H-tetrazol-5-yl)-biphenyl-4-yl] urea;
N-(3,5-Dichloro-phenyl)-N'-[4-bromo-2-(1-H-tetrazol-5-yl)-phenyl] urea;
N-(3,4-Dichloro-phenyl)-N'-[4-bromo-2-(1-H-tetrazol-5-yl)-phenyl] urea;
N-(Naphthalen-1-yl)-N'-[4-bromo-2-(1-H-tetrazol-5-yl)-phenyl] urea;
N-(2-Trifluoromethyl-phenyl)-N'-[4-bromo-2-(1-H-tetrazol-5-yl)-phenyl] urea;
N-(2-Fluoro-phenyl)-N'-[4-bromo-2-(1-H-tetrazol-5-yl)-phenyl] urea;
N-(2-Ethyl-phenyl)-N'-[4-bromo-2-(1-H-tetrazol-5-yl)-phenyl] urea;
or a pharmaceutically acceptable salt thereof.

11. The method according to claim 1, wherein the VRAC modulator has the structure of formula II

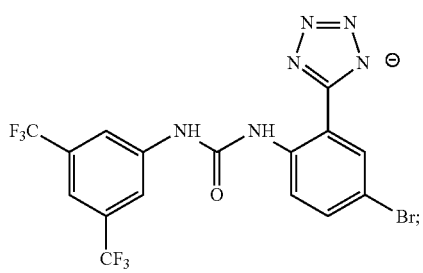

(II)

or a pharmaceutically acceptable salt thereof.

12. The method according to claim 1, wherein the VRAC modulator is in the form of:
 a) tablets or capsules for oral administration; or
 b) a liquid for intravenous administration or continuous infusion.

13. The method according to claim 1, wherein the VRAC modulator is administered through an administration route selected from the group consisting of: oral, rectal, bronchial, nasal, pulmonal, topical, transdermal, vaginal, parenteral, inhalation, and insufflation administration.

14. The method according to claim 1, wherein the VRAC modulator is administered through an administration route selected from the group consisting of:
 a) buccal or sub-lingual;
 b) cutaneous, subcutaneous, intramuscular, intraperitoneal, intravenous, intraarterial, intracerebral, intraocular, or infusion.

15. The method according to claim 1, wherein the cancer is resistant to an anti-cancer agent.

16. The method according to claim 15, wherein resistance is:
 a) de novo resistance; or
 b) acquired resistance.

17. The method according to claim 15, wherein treatment with the VRAC modulator re-sensitises the cancer to the anti-cancer agent.

18. The method according to claim 1, wherein the cancer is a solid tumour.

19. The method according to claim 1, wherein the cancer is metastatic cancer.

* * * * *